US011571498B2

(12) United States Patent
Morgan et al.

(10) Patent No.: US 11,571,498 B2
(45) Date of Patent: *Feb. 7, 2023

(54) DRUG ELUTING MEDICAL DEVICE

(71) Applicant: Covidien LP, Mansfield, MA (US)

(72) Inventors: Terry Morgan, Santa Rosa, CA (US); Beth Sersen, Santa Rosa, CA (US); Daniel Schulz-Jander, Oakland, CA (US); Joseph Traina, Napa, CA (US); Brian Graham, Santa Rosa, CA (US); Carol Sullivan, Litchfield Park, AZ (US); Gerald Hodgkinson, Killingworth, CT (US)

(73) Assignee: Covidien LP, Mansfield, MA (US)

( * ) Notice: Subject to any disclaimer, the term of this patent is extended or adjusted under 35 U.S.C. 154(b) by 145 days.

This patent is subject to a terminal disclaimer.

(21) Appl. No.: 17/106,276

(22) Filed: Nov. 30, 2020

(65) Prior Publication Data

US 2021/0085831 A1 Mar. 25, 2021

Related U.S. Application Data

(63) Continuation of application No. 15/837,498, filed on Dec. 11, 2017, now Pat. No. 10,874,768.

(60) Provisional application No. 62/448,509, filed on Jan. 20, 2017.

(51) Int. Cl.

| | | |
|---|---|---|
| A61F 2/01 | (2006.01) |
| A61L 27/54 | (2006.01) |
| A61L 31/16 | (2006.01) |
| A61P 31/00 | (2006.01) |
| A61B 17/115 | (2006.01) |
| A61B 17/32 | (2006.01) |
| A61L 27/18 | (2006.01) |
| A61L 27/26 | (2006.01) |
| A61L 27/28 | (2006.01) |
| A61L 27/34 | (2006.01) |
| A61L 27/56 | (2006.01) |
| A61L 31/04 | (2006.01) |
| A61L 31/06 | (2006.01) |
| A61L 31/08 | (2006.01) |
| A61L 31/10 | (2006.01) |
| A61L 31/14 | (2006.01) |

(52) U.S. Cl.
CPC .......... *A61L 27/54* (2013.01); *A61B 17/1155* (2013.01); *A61B 17/32* (2013.01); *A61L 27/18* (2013.01); *A61L 27/26* (2013.01); *A61L 27/28* (2013.01); *A61L 27/34* (2013.01); *A61L 27/56* (2013.01); *A61L 31/041* (2013.01); *A61L 31/06* (2013.01); *A61L 31/08* (2013.01); *A61L 31/10* (2013.01); *A61L 31/146* (2013.01); *A61L 31/16* (2013.01); *A61P 31/00* (2018.01); *A61L 2300/416* (2013.01); *A61L 2300/602* (2013.01); *A61L 2300/606* (2013.01); *A61L 2300/802* (2013.01)

(58) Field of Classification Search
CPC .. A61F 2/02; A61F 2/00; A61F 2/0031; A61F 2/0063; A61F 1/10; A61F 2002/016; A61F 2002/018
See application file for complete search history.

(56) References Cited

U.S. PATENT DOCUMENTS

| | | |
|---|---|---|
| 3,054,406 A | 9/1962 | Usher |
| 3,079,606 A | 3/1963 | Bobrov et al. |
| 3,124,136 A | 3/1964 | Usher |
| 3,364,200 A | 1/1968 | Ashton et al. |
| 3,490,675 A | 1/1970 | Green et al. |
| 3,499,591 A | 3/1970 | Green |
| 3,797,494 A | 3/1974 | Zaffaroni |
| 3,939,068 A | 2/1976 | Wendt et al. |
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,605,730 A | 8/1986 | Shalaby et al. |

(Continued)

FOREIGN PATENT DOCUMENTS

| | | |
|---|---|---|
| CA | 2282761 A1 | 9/1998 |
| DE | 1602563 U | 3/1950 |

(Continued)

OTHER PUBLICATIONS

Office Action issued in corresponding Japanese application JP 2018-004711 dated Sep. 3, 2021, together with English language translation (13 pages).

(Continued)

*Primary Examiner* — Micah Paul Young
(74) *Attorney, Agent, or Firm* — Carter, DeLuca & Farrell LLP

(57) ABSTRACT

The present disclosure relates to medical devices, and methods for producing and using the devices. In embodiments, the medical device may be a buttress including a porous substrate possessing a therapeutic layer of a chemotherapeutic agent and optional excipient(s) thereon. By varying the form of chemotherapeutic agents and excipients, the medical devices may be used to treat both the area to which the medical device is attached as well as tissue at a distance therefrom.

20 Claims, 8 Drawing Sheets

(56) References Cited

U.S. PATENT DOCUMENTS

| | | |
|---|---|---|
| 4,626,253 A | 12/1986 | Broadnax, Jr. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,112,496 A | 5/1992 | Dhawan et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,405,072 A | 4/1995 | Zlock et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,645,915 A | 7/1997 | Kranzler et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,871,135 A | 2/1999 | Williamson, IV et al. |
| 5,874,500 A | 2/1999 | Rhee et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,957,363 A | 9/1999 | Heck |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A | 8/2000 | Gabbay |
| 6,142,933 A | 11/2000 | Longo et al. |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,270,530 B1 | 8/2001 | Eldridge et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,399,362 B1 | 6/2002 | Pui et al. |
| 6,436,030 B2 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,568,398 B2 | 5/2003 | Cohen |
| 6,590,095 B1 | 7/2003 | Schleicher et al. |
| 6,592,597 B2 | 7/2003 | Grant et al. |
| 6,605,294 B2 | 8/2003 | Sawhney |
| 6,610,006 B1 | 8/2003 | Amid et al. |
| 6,627,749 B1 | 9/2003 | Kumar |
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,843,252 B2 | 1/2005 | Harrison et al. |
| 6,896,684 B2 | 5/2005 | Monassevitch et al. |
| 6,927,315 B2 | 8/2005 | Heinecke et al. |
| 6,939,358 B2 | 9/2005 | Palacios et al. |
| 6,946,196 B2 | 9/2005 | Foss |
| 6,953,139 B2 | 10/2005 | Milliman et al. |
| 6,959,851 B2 | 11/2005 | Heinrich |
| 7,009,034 B2 | 3/2006 | Pathak et al. |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,210,810 B1 | 5/2007 | Iversen et al. |

(56) References Cited

U.S. PATENT DOCUMENTS

| | | |
|---|---|---|
| 7,214,727 B2 | 5/2007 | Kwon et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,308,998 B2 | 12/2007 | Mastri et al. |
| 7,311,720 B2 | 12/2007 | Mueller et al. |
| 7,328,829 B2 | 2/2008 | Arad et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,464,849 B2 | 12/2008 | Shelton, IV et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,592,418 B2 | 9/2009 | Pathak et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,645,874 B2 | 1/2010 | Saferstein et al. |
| 7,649,089 B2 | 1/2010 | Kumar et al. |
| 7,655,288 B2 | 2/2010 | Bauman et al. |
| 7,662,409 B2 | 2/2010 | Masters |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,673,782 B2 | 3/2010 | Hess et al. |
| 7,708,180 B2 | 5/2010 | Murray et al. |
| 7,709,631 B2 | 5/2010 | Harris et al. |
| 7,717,313 B2 | 5/2010 | Criscuolo et al. |
| 7,722,642 B2 | 5/2010 | Williamson, IV et al. |
| 7,735,703 B2 | 6/2010 | Morgan et al. |
| 7,744,627 B2 | 6/2010 | Orban, III et al. |
| 7,754,002 B2 | 7/2010 | Maase et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 3,038,045 A1 | 10/2011 | Bettuchi et al. |
| 8,028,883 B2 | 10/2011 | Stopek |
| 8,033,483 B2 | 10/2011 | Fortier et al. |
| 8,033,983 B2 | 10/2011 | Chu et al. |
| 3,062,330 A1 | 11/2011 | Prommersberger et al. |
| 8,062,673 B2 | 11/2011 | Figuly et al. |
| 8,083,119 B2 | 12/2011 | Prommersberger |
| 8,091,756 B2 | 1/2012 | Viola |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,177,797 B2 | 5/2012 | Shimoji et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,210,453 B2 | 7/2012 | Hull et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,252,339 B2 | 8/2012 | Figuly et al. |
| 8,252,921 B2 | 8/2012 | Vignon et al. |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,317,790 B2 | 11/2012 | Bell et al. |
| 8,322,590 B2 | 12/2012 | Patel et al. |
| 8,348,126 B2 | 1/2013 | Olson et al. |
| 8,348,130 B2 | 1/2013 | Shah et al. |
| 8,365,972 B2 | 2/2013 | Aranyi et al. |
| 8,367,089 B2 | 2/2013 | Wan et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,408,480 B2 | 4/2013 | Hull et al. |
| 8,413,869 B2 | 4/2013 | Heinrich |
| 8,413,871 B2 | 4/2013 | Racenet et al. |
| 8,418,909 B2 | 4/2013 | Kostrzewski |
| 8,424,742 B2 | 4/2013 | Bettuchi |
| 8,449,603 B2 | 5/2013 | Weber et al. |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,470,360 B2 | 6/2013 | McKay |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,518,440 B2 | 8/2013 | Blaskovich et al. |
| 8,529,600 B2 | 9/2013 | Woodard, Jr. et al. |
| 8,540,128 B2 | 9/2013 | Shelton, IV et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,579,990 B2 | 11/2013 | Priewe |
| 8,584,920 B2 | 11/2013 | Hodgkinson |
| 8,590,762 B2 | 11/2013 | Hess et al. |
| 8,616,430 B2 | 12/2013 | Stopek et al. |
| 8,617,132 B2 | 12/2013 | Golzarian et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,678,263 B2 | 3/2014 | Viola |
| 8,679,137 B2 | 3/2014 | Bauman et al. |
| 8,684,250 B2 | 4/2014 | Bettuchi et al. |
| 8,701,958 B2 | 4/2014 | Shelton, IV et al. |

(56) References Cited

U.S. PATENT DOCUMENTS

| | | | |
|---|---|---|---|
| 8,721,703 B2 | 5/2014 | Fowler |
| 8,727,197 B2 | 5/2014 | Hess et al. |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,827,133 B2 | 9/2014 | Shelton, IV et al. |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,900,616 B2 | 12/2014 | Belcheva et al. |
| 8,920,443 B2 | 12/2014 | Hiles et al. |
| 8,920,444 B2 | 12/2014 | Hiles et al. |
| 8,939,344 B2 | 1/2015 | Olson et al. |
| 8,956,390 B2 | 2/2015 | Shah et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,871 B2 | 8/2015 | Milliman et al. |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,768 B2 | 5/2016 | Shelton, IV |
| 9,326,773 B2 | 5/2016 | Casasanta, Jr. et al. |
| 9,328,111 B2 | 5/2016 | Zhou et al. |
| 9,345,479 B2 | 5/2016 | Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | Stopek et al. |
| 9,386,988 B2 | 7/2016 | Baxter, III et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,463,260 B2 | 10/2016 | Stopek |
| 9,486,215 B2 | 11/2016 | Olson et al. |
| 9,492,170 B2 | 11/2016 | Bear et al. |
| 9,504,470 B2 | 11/2016 | Milliman |
| 9,517,164 B2 | 12/2016 | Vitaris et al. |
| 9,572,576 B2 | 2/2017 | Hodgkinson et al. |
| 9,585,657 B2 | 3/2017 | Shelton, IV et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,636,850 B2 | 5/2017 | Stopek et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,687,262 B2 | 6/2017 | Rousseau et al. |
| 9,693,772 B2 | 7/2017 | Ingmanson et al. |
| 9,708,184 B2 | 7/2017 | Chan et al. |
| 9,770,245 B2 | 9/2017 | Swayze et al. |
| 9,775,617 B2 | 10/2017 | Carter et al. |
| 9,782,173 B2 | 10/2017 | Mozdzierz |
| 10,874,768 B2 * | 12/2020 | Morgan .................. A61L 27/26 |
| 2002/0091397 A1 | 7/2002 | Chen |
| 2002/0151911 A1 | 10/2002 | Gabbay |
| 2003/0065345 A1 | 4/2003 | Weadock |
| 2003/0078209 A1 | 4/2003 | Schmidt |
| 2003/0083676 A1 | 5/2003 | Wallace |
| 2003/0125676 A1 | 7/2003 | Swenson et al. |
| 2003/0181927 A1 | 9/2003 | Wallace |
| 2003/0208231 A1 | 11/2003 | Williamson et al. |
| 2004/0092912 A1 | 5/2004 | Jinno et al. |
| 2004/0107006 A1 | 6/2004 | Francis et al. |
| 2004/0254590 A1 | 12/2004 | Hoffman et al. |
| 2004/0260272 A1 | 12/2004 | Friedman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0149073 A1 | 7/2005 | Arani et al. |
| 2005/0283256 A1 | 12/2005 | Sommerich et al. |
| 2006/0008505 A1 | 1/2006 | Brandon |
| 2006/0121266 A1 | 6/2006 | Fandel et al. |
| 2006/0173470 A1 | 8/2006 | Oray et al. |
| 2006/0190027 A1 | 8/2006 | Downey |
| 2007/0034669 A1 | 2/2007 | de la Torre et al. |
| 2007/0203510 A1 | 8/2007 | Bettuchi |
| 2007/0212394 A1 | 9/2007 | Reyes et al. |
| 2007/0224235 A1 | 9/2007 | Tenney et al. |
| 2007/0243227 A1 | 10/2007 | Gertner |
| 2007/0246505 A1 | 10/2007 | Pace-Floridia et al. |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0140115 A1 | 6/2008 | Stopek |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0216855 A1 | 9/2008 | Nasca |
| 2008/0220047 A1 | 9/2008 | Sawhney et al. |
| 2008/0286325 A1 | 11/2008 | Reyes et al. |
| 2008/0290134 A1 | 11/2008 | Bettuchi et al. |
| 2009/0001121 A1 | 1/2009 | Hess et al. |
| 2009/0001130 A1 | 1/2009 | Hess et al. |
| 2009/0031842 A1 | 2/2009 | Kawai et al. |
| 2009/0123521 A1 * | 5/2009 | Weber .................... A61L 27/30 |
| | | 424/426 |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0218384 A1 | 9/2009 | Aranyi |
| 2009/0277944 A9 | 11/2009 | Dalessandro et al. |
| 2010/0016855 A1 | 1/2010 | Ramstein et al. |
| 2010/0016888 A1 | 1/2010 | Calabrese et al. |
| 2010/0076489 A1 | 3/2010 | Stopek et al. |
| 2010/0087840 A1 | 4/2010 | Ebersole et al. |
| 2010/0147921 A1 | 6/2010 | Olson |
| 2010/0147922 A1 | 6/2010 | Olson |
| 2010/0174253 A1 | 7/2010 | Cline et al. |
| 2010/0203151 A1 | 8/2010 | Hiraoka |

(56) References Cited

U.S. PATENT DOCUMENTS

| | | |
|---|---|---|
| 2010/0243707 A1 | 9/2010 | Olson et al. |
| 2010/0331859 A1 | 12/2010 | Omori |
| 2011/0034910 A1 | 2/2011 | Ross et al. |
| 2011/0089220 A1 | 4/2011 | Ingmanson et al. |
| 2011/0125138 A1 | 5/2011 | Malinouskas et al. |
| 2011/0166673 A1 | 7/2011 | Patel et al. |
| 2011/0293690 A1 | 12/2011 | Griffin et al. |
| 2011/0295200 A1 | 12/2011 | Speck et al. |
| 2012/0080336 A1 | 4/2012 | Shelton, IV et al. |
| 2012/0171383 A1 | 7/2012 | Christensen et al. |
| 2012/0197272 A1 | 8/2012 | Oray et al. |
| 2012/0241491 A1 | 9/2012 | Aldridge et al. |
| 2012/0241493 A1 | 9/2012 | Baxter, III et al. |
| 2012/0253298 A1 | 10/2012 | Henderson et al. |
| 2012/0316633 A1 | 12/2012 | Flanagan et al. |
| 2013/0153636 A1 | 6/2013 | Shelton, IV et al. |
| 2013/0153641 A1 | 6/2013 | Shelton, IV et al. |
| 2013/0209659 A1 | 8/2013 | Racenet et al. |
| 2013/0256380 A1 | 10/2013 | Schmid et al. |
| 2014/0048580 A1 | 2/2014 | Merchant et al. |
| 2014/0131418 A1 | 5/2014 | Kostrzewski |
| 2014/0239047 A1 | 8/2014 | Hodgkinson et al. |
| 2015/0041347 A1 | 2/2015 | Hodgkinson |
| 2015/0133995 A1 | 5/2015 | Shelton, IV et al. |
| 2015/0209045 A1 | 7/2015 | Hodgkinson et al. |
| 2015/0305743 A1 | 10/2015 | Casasanta et al. |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0100834 A1 | 4/2016 | Viola et al. |
| 2016/0106430 A1 | 4/2016 | Carter et al. |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0256166 A1 | 9/2016 | Stopek et al. |
| 2016/0270793 A1 | 9/2016 | Carter et al. |
| 2016/0310143 A1 | 10/2016 | Bettuchi |
| 2016/0317720 A1 | 11/2016 | Ostapoff et al. |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0150967 A1 | 6/2017 | Hodgkinson et al. |

FOREIGN PATENT DOCUMENTS

| | | |
|---|---|---|
| DE | 19924311 A1 | 11/2000 |
| EP | 0327022 A2 | 8/1989 |
| EP | 0594148 A1 | 4/1994 |
| EP | 2228082 A2 | 9/2010 |
| EP | 2724734 A2 | 4/2014 |
| EP | 3087931 A2 | 11/2016 |
| JP | 2000166933 A | 6/2000 |
| JP | 2002202213 A | 7/2002 |
| JP | 2007124166 A | 5/2007 |
| JP | 2010214132 A | 9/2010 |
| WO | 9005489 A1 | 5/1990 |
| WO | 95/16221 A1 | 6/1995 |
| WO | 98/38923 A1 | 9/1998 |
| WO | 9926826 A2 | 6/1999 |
| WO | 0010456 A1 | 3/2000 |
| WO | 0016684 A1 | 3/2000 |
| WO | 2007106441 A2 | 9/2007 |
| WO | 2010021757 A2 | 2/2010 |
| WO | 2010075298 A2 | 7/2010 |
| WO | 2010079218 A2 | 7/2010 |
| WO | 2011119159 A1 | 9/2011 |
| WO | 2015137962 A1 | 9/2015 |
| WO | 2016205652 A1 | 12/2016 |
| WO | 2017046193 A1 | 3/2017 |

OTHER PUBLICATIONS

European Search Report corresponding to EP 12 16 5609.4, completed Jul. 5, 2012 and dated Jul. 13, 2012; (8 pp).
European Search Report corresponding to EP 12 15 8861.0, completed Jul. 17, 2012 and dated Jul. 24, 2012; (9 pp).
European Search Report corresponding to EP 12 16 5878.5, completed Jul. 24, 2012 and dated Aug. 6, 2012; (8 pp).
Extended European Search Report corresponding to EP 12 19 1035.0, completed Jan. 11, 2013 and dated Jan. 18, 2013; (7 pp).
Extended European Search Report corresponding to EP 12 18 6175.1, completed Jan. 15, 2013 and dated Jan. 23, 2013; (7 pp).
Extended European Search Report corresponding to EP 12 19 1114.3, completed Jan. 23, 2013 and dated Jan. 31, 2013; (10 pp).
Extended European Search Report corresponding to EP 12 19 2224.9, completed Mar. 14, 2013 and dated Mar. 26, 2013; (8 pp).
Extended European Search Report corresponding to EP 12 19 6904.2, completed Mar. 28, 2013 and dated Jul. 26, 2013; (8 pp).
Extended European Search Report corresponding to EP 12 19 6911.7, completed Apr. 18, 2013 and dated Apr. 24, 2013; (8 pp).
Extended European Search Report corresponding to EP 07 00 5842.5, completed May 13, 2013 and dated May 29, 2013; (7 pp).
Extended European Search Report corresponding to EP 12 19 8776.2, completed May 16, 2013 and dated May 27, 2013; (8 pp).
Extended European Search Report corresponding to EP 12 19 8749.9, completed May 21, 2013 and dated May 31, 2013; (8 pp).
Extended European Search Report corresponding to EP 13 15 6297.7, completed Jun. 4, 2013 and dated Jun. 13, 2013I; (7 pp).
Extended European Search Report corresponding to EP 13 17 3985.6, completed Aug. 19, 2013 and dated Aug. 28, 2013; (6 pp).
Extended European Search Report corresponding to EP 13 17 3986.4, completed Aug. 20, 2013 and dated Aug. 29, 2013; (6 pp).
Extended European Search Report corresponding to EP 13 17 7437.4, completed Sep. 11, 2013 and dated Sep. 19, 2013; 6 pages.
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 18 2911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresponding to EP 13 19 2111.6, completed Feb. 13, 2014 and dated Feb. 27, 2014; (10 pp).
Extended European Search Report corresponding to EP 13 19 5919.9, completed Feb. 10, 2014 and dated Mar. 3, 2014; (7 pp).
Extended European Search Report corresponding to EP 08 72 6500.5, completed Feb. 20, 2014 and dated Mar. 3, 2014; (7 pp).
Extended European Search Report corresponding to EP 13 19 5019.8, completed Mar. 14, 2014 and dated Mar. 24, 2014; (7 pp).
Extended European Search Report corresponding to EP 13 19 6816.6, completed Mar. 28, 2014 and dated Apr. 9, 2014; (9 pp).
Extended European Search Report corresponding to EP 13 19 7958.5, completed Apr. 4, 2014 and dated Apr. 15, 2014; (8 pp).
Extended European Search Report corresponding to EP 13 19 4995.0, completed Jun. 5, 2014 and dated Jun. 16, 2014; (5 pp).
Extended European Search Report corresponding to EP 14 15 7195.0, completed Jun. 5, 2014 and dated Jun. 18, 2014; (9 pp).
Extended European Search Report corresponding to EP 14 15 6342.9, completed Jul. 22, 2014 and dated Jul. 29, 2014; (8 pp).

(56) References Cited

OTHER PUBLICATIONS

Extended European Search Report issued in Appl. No. EP 18152491.9 dated Jun. 6, 2018 (12 pages).
Extended European Search Report issued in Appl. No. EP 18183850.9-1109 dated Dec. 20, 2018 (8 pages).
European Examination Report issued in corresponding Appl. No. EP 18152491.9 dated Jun. 17, 2020 (9 pages).
Extended European Search Report corresponding to EP 14 16 9739 1, completed Aug. 19, 2014 and dated Aug. 29, 2014; (7 pp).
Extended European Search Report corresponding to EP 14 15 7997 9, completed Sep. 9, 2014 and dated Sep. 17, 2014; (8 pp).
Extended European Search Report corresponding to EP 14 16 8904 2, completed Sep. 10, 2014 and dated Sep. 18, 2014; (8 pp).
Extended European Search Report corresponding to EP 13 19 4995 0, completed Jun. 5, 2014 and dated Oct. 13, 2014; (10 pp).
Extended European Search Report corresponding to EP 13 15 4571 7, completed Oct. 10, 2014 and dated Oct. 20, 2014; (8 pp).
Extended European Search Report corresponding to EP 14 18 1125 7, completed Oct. 16, 2014 and dated Oct. 24, 2014; (7 pp).
Extended European Search Report corresponding to EP 14 18 1127 3, completed Oct. 16, 2014 and dated Nov. 10, 2014; (8 pp).
Extended European Search Report corresponding to EP 14 19 0419 3, completed Mar. 24, 2015 and dated Mar. 30, 2015; (6 pp).
European Office Action corresponding to counterpart Int'l Appln No. EP 12 198 776.2 dated Apr. 7, 2015.
European Office Action corresponding to counterpart Int'l Appln No. EP 13 156 297.7 dated Apr. 10, 2015.
Australian Examination Report No. 1 corresponding to counterpart Int'l Appln No. AU 2011250822 dated May 18, 2015.
European Office Action corresponding to counterpart Int'l Appln No. EP 12 186 175.1 dated Jun. 1, 2015.
Chinese Office Action corresponding to counterpart Int'l Appln No. CN 201010517292.8 dated Jun. 2, 2015.
Extended European Search Report corresponding to counterpart Int'l Appln No. EP 14 17 48145 dated Jun. 9, 2015.
Australian Examination Report No. 1 corresponding to counterpart Int'l Appln No. AU 2014200584 dated Jun. 15, 2015.
European Office Action corresponding to counterpart Int'l Appln No. EP 13 180 881.8 dated Jun. 19, 2015.
European Office Action corresponding to counterpart Int'l Appln No. EP 14 157 195.0 dated Jul. 2, 2015.
Extended European Search Report corresponding to counterpart Int'l Appln No. EP 12 19 6902.6 dated Aug. 6, 2015.
Extended European Search Report corresponding to counterpart Int'l Appln No. EP 14 15 2060.1 dated Aug. 14, 2015.
Chinese Office Action corresponding to counterpart Int'l Appln No. CN 201210129787.2 dated Aug. 24, 2015.
Canadian Office Action corresponding to counterpart Int'l Appln. No. CA 2,665,206 dated Nov. 19, 2013.
Chinese Notification of Reexamination corresponding to counterpart Int'l Appln. No. CN 201010517292.8 dated Jun. 2, 2015.
Japanese Office Action corresponding to counterpart Int'l Appln. No. JP 2014-216989 dated Sep. 11, 2015.
Canadian First Office Action corresponding to counterpart Int'l Appln. No. CA 2,686,105 dated Sep. 17, 2015.
Japanese Office Action corresponding to counterpart Int'l Appln. No. JP 2012-040188 dated Oct. 21, 2015.
European Communication corresponding to counterpart Int'l Appln. No. EP 13 17 6895.4 dated Nov. 5, 2015.
Chinese First Office Action corresponding to counterpart Int'l Appln. No. CN 201210544552 dated Nov. 23, 2015.
Chinese First Office Action corresponding to counterpart Int'l Appln. No. CN 201210545228 dated Nov. 30, 2015.
Extended European Search Report corresponding to counterpart Int'l Appln. No. EP 15 18 0491.1 dated Dec. 9, 2015.
Extended European Search Report corresponding to counterpart Int'l Appln. No. EP 15 18 3819.0 dated Dec. 11, 2015.
Canadian Office Action corresponding to counterpart Int'l Appln. No. CA 2,697,819 dated Jan. 6, 2016.
Canadian Office Action corresponding to counterpart Int'l Appln. No. CA 2,696,419 dated Jan. 14, 2016.
European Office Action corresponding to counterpart Int'l Appln. No. EP 12 19 8776.2 dated Jan. 19, 2016.
Extended European Search Report corresponding to counterpart Int'l Appln. No. EP 15 17 4146.9 dated Jan. 20, 2016.
Chinese First Office Action corresponding to counterpart Int'l Appln. No. CN 201310353628.5 dated Jan. 25, 2016.
Extended European Search Report corresponding to counterpart Int'l Appln. No. EP 12 19 6912.5 dated Feb. 1, 2016.
Japanese Office Action corresponding to counterpart Int'l Appln. No. JP 2012-098903 dated Feb. 22, 2016.
Extended European Search Report corresponding to counterpart Int'l Appln. No. EP 12 19 8753.1 dated Feb. 24, 2016.
Chinese First Office Action corresponding to counterpart Int'l Appln. No. CN 201410449019.4 dated Mar. 30, 2016.
Extended European Search Report corresponding to counterpart Int'l Appln. No. EP 16150232.3, dated Apr. 12, 2016.
European Office Action corresponding to counterpart Int'l Appln. No. EP 11 18 3256.4 dated Apr. 20, 2016.
Australian Examination Report No. 1 corresponding to counterpart Int'l Appln. No. AU 2012244169 dated May 10, 2016.
European Office Action corresponding to counterpart Int'l Appln. No. EP 10 25 0715.9 dated May 12, 2016.
Chinese First Office Action corresponding to counterpart Int'l Appln. No. CN 201410778512.0 dated May 13, 2016.
Australian Examination Report No. 1 corresponding to counterpart Int'l Appln. No. AU 2012227358 dated May 16, 2016.
Japanese Office Action corresponding to counterpart Int'l Appln. No. JP 2012-040188 dated May 17, 2016.
Australian Examination Report No. 1 corresponding to counterpart Int'l Appln. No. AU 2012244380 dated May 20, 2016.
Australian Examination Report No. 1 corresponding to counterpart Int'l Appln. No. AU 2014227480 dated May 21, 2016.
Australian Examination Report No. 1 corresponding to counterpart Int'l Appln. No. AU 2012254977 dated May 30, 2016.
European Office Action corresponding to counterpart Int'l Appln. No. EP 14 17 2681.0 dated May 13, 2016.
Extended European Search Report corresponding to counterpart Int'l Appln. No. EP 16 15 3647.9 dated Jun. 3, 2016.
Chinese Office Action corresponding to counterpart Int'l Appln. No. CN 201210545228 dated Jun. 29, 2016.
Japanese Office Action corresponding to counterpart Int'l Appln. No. JP 2012-250058 dated Jun. 29, 2016.
European Office Action corresponding to counterpart Int'l Appln. No. EP 14 15 7997.9 dated Jun. 29, 2016.
Canadian Office Action corresponding to counterpart Int'l Appln. No. CA 2,712,617 dated Jun. 30, 2016.
Chinese First Office Action corresponding to counterpart Int'l Appln. No. CN 2013103036903 dated Jun. 30, 2016.
Australian Patent Examination Report No. 1 corresponding to counterpart Int'l Appln No. AU 2012250278 dated Jul. 10, 2016.
Australian Patent Examination Report No. 1 corresponding to counterpart Int'l Appln. No. AU 2012244382 dated Jul. 10, 2016.
Japanese Office Action corresponding to counterpart Int'l Appln. No. JP 2012-255242 dated Jul. 26, 2016.
Japanese Office Action corresponding to counterpart Int'l Appln. No. JP 2012-268668 dated Jul. 27, 2016.
European Office Action corresponding to counterpart Int'l Appln. No. EP 14 15 2060.1 dated Aug. 4, 2016.
European Office Action corresponding to counterpart Int'l Appln. No. EP 12 16 5609.4 dated Aug. 5, 2016.
European Office Action corresponding to counterpart Int'l Appln. No. EP 15 15 2392.5 dated Aug. 8, 2016.
Japanese Office Action corresponding to counterpart Int'l Appln. No. JP 2013-003624 dated Aug. 25, 2016.
Australian Patent Examination Report No. 1 corresponding to counterpart Int'l Appln. No. AU 2012261752 dated Sep. 3, 2016.
Japanese Office Action corresponding to counterpart Int'l Appln. No. JP 2014-252703 dated Sep. 26, 2016.
European Office Action corresponding to counterpart Int'l Appln. No. EP 12 19 8776.2 dated Sep. 12, 2016.

(56) References Cited

OTHER PUBLICATIONS

Japanese Office Action corresponding to counterpart Int'l Appln. No. JP 2013-000321 dated Sep. 13, 2016.
Chinese Second Office Action corresponding to counterpart Int'l Appln. No. CN 201310353628.5 dated Sep. 26, 2016.
European Office Action corresponding to counterpart Int'l Appln. No. EP 12 15 2541.4 dated Sep. 27, 2016.
Australian Patent Examination Report No. 1 corresponding to counterpart Int'l Appln. No. AU 2012268923 dated Sep. 28, 2016.
Chinese First Office Action corresponding to counterpart Int'l Appln. No. CN 201310706871.0 dated Dec. 16, 2016.
Chinese First Office Action corresponding to counterpart Int'l Appln. No. CN 201310646606.8 dated Dec. 23, 2016.
Japanese Office Action corresponding to counterpart Int'l Appln. No. JP 2013-000321 dated Jan. 4, 2017.
Extended European Search Report corresponding to counterpart Int'l Appln. No. EP 16 16 6367.9 dated Jan. 16, 2017.
Australian Examination Report No. 1 corresponding to counterpart Int'l Appln. No. AU 2013206777 dated Feb. 1, 2017.
Chinese Second Office Action corresponding to counterpart Int'l Appln. No. CN 201310303690.3 dated Feb. 23, 2017.
Japanese Office Action corresponding to counterpart Int'l Appln. No. JP 2013-175379 dated Mar. 1, 2017.
Chinese First Office Action corresponding to counterpart Int'l Appln. No. CN 201410028462.4 dated Mar. 2, 2017.
Chinese First Office Action corresponding to counterpart Int'l Appln. No. CN 201410084070 dated Mar. 13, 2017.
Extended European Search Report corresponding to counterpart Int'l Appln. No. EP 16 19 6549.6 dated Mar. 17, 2017.
Japanese Office Action corresponding to counterpart Int'l Appln. No. JP 2013-147701 dated Mar. 21, 2017.
Australian Examination Report No. 1 corresponding to counterpart Int'l Appln. No. AU 2013206804 dated Mar. 21, 2017.
Australian Examination Report No. 1 corresponding to counterpart Int'l Appln. No. AU 2013211499 dated May 4, 2017.
Australian Examination Report No. 1 corresponding to counterpart Int'l Appln. No. AU 2014201008 dated May 23, 2017.
European Search Report corresponding to EP 06 00 4598, completed Jun. 22, 2006; (2 pp).
European Search Report corresponding to EP 06 01 6962.0, completed Jan. 3, 2007 and dated Jan. 11, 2007; (10 pp).
International Search Report corresponding to International Application No. PCT/US2005/036740, completed Feb. 20, 2007 and dated Mar. 23, 2007; (8 pp).
International Search Report corresponding to International Application No. PCT/US2007/022713, completed Apr. 21, 2008 and dated May 15, 2008; (1 p).
International Search Report corresponding to International Application No. PCT/US2008/002981, completed Jun. 9, 2008 and dated Jun. 26, 2008; (2 pp).
European Search Report corresponding to EP 08 25 1779, completed Jul. 14, 2008 and dated Jul. 23, 2008; (5 pp).
European Search Report corresponding to EP 08 25 1989.3, completed Mar. 11, 2010 and dated Mar. 24, 2010; (6 op).
European Search Report corresponding to EP 10 25 0639.1, completed Jun. 17, 2010 and dated Jun. 28, 2010; (7 pp).
European Search Report corresponding to EP 10 25 0715.9, completed Jun. 30, 2010 and dated Jul. 20, 2010; (3 pp).
European Search Report corresponding to EP 05 80 4382.9, completed Oct. 5, 2010 and dated Oct. 12, 2010; (3 pp).
European Search Report corresponding to EP 09 25 2897.5, completed Feb. 7, 2011 and dated Feb. 15, 2011; (3 pp).
European Search Report corresponding to EP 10 25 0642.5, completed Mar. 25, 2011 and dated Apr. 4, 2011; (4 pp).
European Search Report corresponding to EP 12 15 2229.6, completed Feb. 23, 2012 and dated Mar. 1, 2012; (4 pp).
European Search Report corresponding to EP 12 15 0511.9, completed Apr. 16, 2012 and dated Apr. 24, 2012; (7 pp).
European Search Report corresponding to EP 12 15 2541 4, completed Apr. 23, 2012 and dated May 3, 2012; (10 pp).
Final Office Action issued in corresponding Japanese Application No. 2018-004711, dated Jun. 24, 2022, together with English language translation (15 pages).

* cited by examiner

| Buttress | Section 1 | | | Section 4 | | | Section 7 | | |
|---|---|---|---|---|---|---|---|---|---|
| | 1a-BA | 1m-BA | 1p-BA | 4a-BA | 4m-BA | 4p-BA | 7a-BA | 7m-BA | 7p-BA |
| | 1a-histo | 1m-histo | 1p-histo | 4a-histo | 4m-histo | 4p-histo | 7a-histo | 7m-histo | 7p-histo |
| | Section 2 | | | Section 5 | | | Section 8 | | |
| | 2a-BA | 2m-BA | 2p-BA | 5a-BA | 5m-BA | 5p-BA | 8a-BA | 8m-BA | 8p-BA |
| | 2a-histo | 2m-histo | 2p-histo | 5a-histo | 5m-histo | 5p-histo | 8a-histo | 8m-histo | 8p-histo |
| | Section 3 | | | Section 6 | | | Section 9 | | |
| | 3a-BA | 3m-BA | 3p-BA | 6a-BA | 6m-BA | 6p-BA | 9a-BA | 9m-BA | 9p-BA |
| | 3a-histo | 3m-histo | 3p-histo | 6a-histo | 6m-histo | 6p-histo | 9a-histo | 9m-histo | 9p-histo |
| | < Anterior Posterior > | | | < Anterior Posterior > | | | < Anterior Posterior > | | |

A=Anterior, m=mid, p=posterior.
BA samples to be placed in labeled cryotubes, flash frozen, and stored at -20°C.
Histology samples to be placed in labeled tissue cassettes and immersed in 10% NBF.

*Fig. 5*

DRUG ELUTING MEDICAL DEVICE

CROSS-REFERENCE TO RELATED APPLICATION

This application is a continuation of U.S. application Ser. No. 15/837,498, filed Dec. 11, 2017, which claims the benefit of and priority to U.S. Provisional Patent Application No. 62/448,509 filed Jan. 20, 2017, the entire disclosures of each of which are incorporated by reference herein.

BACKGROUND

The present disclosure relates to medical devices, including surgical devices such as buttresses, for use with wound closure devices. Medical devices formed of the materials of the present disclosure are capable of delivering drugs to a patient.

Surgical stapling instruments are employed by surgeons to sequentially or simultaneously apply one or more rows of fasteners, e.g., staples or two-part fasteners, to body tissue for the purpose of joining segments of body tissue together. Such instruments generally include a pair of jaws or finger-like structures between which the body tissue to be joined is placed. When the stapling instrument is actuated, or "fired", longitudinally moving firing bars contact staple drive members in one of the jaws. The staple drive members push the surgical staples through the body tissue and into an anvil in the opposite jaw, which forms the staples. If tissue is to be removed or separated, a knife blade can be provided in the jaws of the device to cut the tissue between the lines of staples.

When stapling certain tissue, such as lung, esophageal, intestinal, duodenal, and vascular tissues, or relatively thin or fragile tissues, it may be desirable to seal the staple line against air or fluid leakage. Preventing or reducing air or fluid leakage can significantly decrease post-operative recovery time. Additionally, it may be desirable to reinforce the staple line against the tissue to prevent tears in the tissue or pulling of the staples through the tissue. One method of preventing these tears involves the placement of a biocompatible fabric reinforcing material, sometimes referred to herein, in embodiments, as a "buttress" material, between the staple and the underlying tissue.

For some surgical procedures, it may also be desirable to introduce therapeutic agents at the site of treatment. For example, low dose radioisotope brachytherapy seeds can be implanted into a patient to treat micrometastatic cancer cells that may be present in tissue near the site of tumor transection in lung, bowel, or other organs.

Improved surgical repair materials, capable of use as buttresses for sealing and/or reinforcing staple lines against tissue, and improved methods for introducing therapeutic agents to a patient, remain desirable.

SUMMARY

The present disclosure relates to medical devices, including surgical buttresses, which can be used with tissue fixation devices, and methods of using the same. Other medical devices not used with tissue fixation devices are contemplated as well, such as tissue supports or other structures.

In embodiments, a medical device of the present disclosure includes a porous substrate and a therapeutic layer on at least a portion of the porous substrate. The therapeutic layer includes a chemotherapeutic agent alone or in combination with an excipient such as 2-hydroxypropyl-beta-cyclodextrin, methyl-ß-cyclodextrin, sodium dodecyl sulfate, octyl glucoside, sorbitan monooleate, sorbitan monolaurate, polyethoxylated fatty acid esters of sorbitan, sodium chloride, urea, oleic acid, citric acid, ascorbic acid, butylated hydroxytoluene, D-sorbitol, and combinations thereof, wherein the therapeutic layer has a surface to volume ratio from about 500 $mm^{-1}$ to about 90,000 $mm^{-1}$. A very high surface to volume ration for the therapeutic layer, providing a very high surface area for eluding the chemotherapeutic agent, while maintaining a low percentage of the weight of the coated buttress has been achieved. In any of the embodiments disclosed herein, the therapeutic layer can have the chemotherapeutic agent without an excipient.

In some embodiments, the chemotherapeutic agent may be paclitaxel and derivatives thereof, docetaxel and derivatives thereof, abraxane, tamoxifen, cyclophosphamide, actinomycin, bleomycin, dactinomycin, daunorubicin, doxorubicin, doxorubicin hydrochloride, epirubicin, mitomycin, methotrexate, fluorouracil, gemcitabine, gemcitabine hydrochloride, carboplatin, carmustine, methyl-CCNU, cisplatin, etoposide, camptothecin and derivatives thereof, phenesterine, vinblastine, vincristine, goserelin, leuprolide, interferon alfa, retinoic acid, nitrogen mustard alkylating agents, piposulfan, vinorelbine, irinotecan, irinotecan hydrochloride, vinblastine, pemetrexed, sorafenib tosylate, everolimus, erlotinib hydrochloride, sunitinib malate, capecitabine oxaliplatin, leucovorin calcium, bevacizumab, cetuximab, ramucirumab, trastuzumab, and combinations thereof.

In certain embodiments, the chemotherapeutic agent includes a polymorph of paclitaxel. Suitable polymorphs of paclitaxel include amorphous paclitaxel, crystalline paclitaxel dihydrate, anhydrous paclitaxel, and combinations thereof.

In some embodiments, the paclitaxel is a combination of amorphous paclitaxel and crystalline paclitaxel dihydrate. In embodiments, the amorphous paclitaxel is released from the medical device over a period of time from about 24 hours to about 168 hours, and the crystalline paclitaxel dihydrate is released from the medical device over a period of time from about 1 week to about 6 weeks.

In embodiments, the excipient includes urea, methyl-ß-cyclodextrin, oleic acid, polysorbate 80, D-sorbitol, octylglucoside, and combinations thereof. In any of the embodiments disclosed herein, the therapeutic layer includes a chemotherapeutic agent without an excipient.

In certain embodiments, the medical device includes surgical buttresses, hernia patches, staples, tacks, stents, and tissue scaffolds.

Other medical devices of the present disclosure include a porous substrate and a therapeutic layer on at least a portion of the porous substrate, the therapeutic layer including amorphous paclitaxel and crystalline paclitaxel dihydrate alone or in combination with an excipient such as urea, methyl-ß-cyclodextrin, oleic acid, polysorbate 80, D-sorbitol, octylglucoside, and combinations thereof. The therapeutic layer has a surface to volume ratio from about 500 $mm^{-1}$ to about 90,000 $mm^{-1}$.

In embodiments, the amorphous paclitaxel is released from the medical device over a period of time from about 24 hours to about 168 hours, and the crystalline paclitaxel dihydrate is released from the medical device over a period of time from about 1 week to about 6 weeks.

In some embodiments, the excipient is present in an amount from about 0.014% to about 14% by weight of the coated buttress.

In certain embodiments, the amorphous paclitaxel and crystalline paclitaxel dihydrate are present in an amount from about 0.1% to about 50% by weight of the coated buttress.

In embodiments, the medical device has a pore volume from about 65% to about 85%.

Methods for treating tissue with these medical devices are also provided. Where the medical device is a buttress, the method includes applying the medical device to tissue with a fixation device such as staples, tacks, clips, sutures, adhesives, and combinations thereof.

Methods for treating cancer with these devices are also provided. In embodiments, a method of treating cancer, in accordance with the present disclosure includes introducing to a patient a surgical stapler having a buttress thereon, the buttress including a coating of a drug; and using the stapler to remove an undesired portion of an organ and emplace the buttress in a remaining portion of the organ, including stapling the buttress to tissue and cutting the tissue.

In embodiments, the stapler is used on the lung.

In some embodiments, the buttress used in the method is made from a non-woven material coated with a chemotherapy drug.

In certain embodiments, the chemotherapy drug used in the method includes paclitaxel and derivatives thereof, docetaxel and derivatives thereof, abraxane, tamoxifen, cyclophosphamide, actinomycin, bleomycin, dactinomycin, daunorubicin, doxorubicin, doxorubicin hydrochloride, epirubicin, mitomycin, methotrexate, fluorouracil, gemcitabine, gemcitabine hydrochloride, carboplatin, carmustine, methyl-CCNU, cisplatin, etoposide, camptothecin and derivatives thereof, phenesterine, vinblastine, vincristine, goserelin, leuprolide, interferon alfa, retinoic acid, nitrogen mustard alkylating agents, piposulfan, vinorelbine, irinotecan, irinotecan hydrochloride, vinblastine, pemetrexed, sorafenib tosylate, everolimus, erlotinib hydrochloride, sunitinib malate, capecitabine oxaliplatin, leucovorin calcium, bevacizumab, cetuximab, ramucirumab, trastuzumab, and combinations thereof.

In embodiments, the coating on the buttress used in the method does not include an excipient.

In embodiments, the buttress used in the method is a non-woven surgical buttress formed from fibers of polyglycolic acid, polylactic acid, or glycolide trimethylene carbonate. In some embodiments, the non-woven material is porous.

In certain embodiments, the thickness of the buttress used in the method is from about 0.05 mm to about 0.5 mm.

In embodiments, the drug used in the method is paclitaxel. In some embodiments, the paclitaxel is amorphous. In other embodiments, the drug includes amorphous paclitaxel and crystalline paclitaxel.

In embodiments, medical devices of the present disclosure, such as a buttress, include a porous substrate and a therapeutic layer on at least a portion of the porous substrate, the therapeutic layer including a chemotherapeutic agent, the therapeutic layer having a surface to volume ratio from about 1,100 $mm^{-1}$ to about 87,000 $mm^{-1}$, wherein the therapeutic agent is present in amounts from about 1% to about 10% by weight of the coated buttress. In some embodiments, the therapeutic layer does not include any additional excipients.

BRIEF DESCRIPTION OF THE DRAWINGS

Embodiments of the presently disclosed specimen retrieval device are described herein with reference to the drawings wherein:

FIG. 5 is a depiction of a lung sectioning scheme for sampling tissue adjacent a buttress of the present disclosure after its placement in a dog;

DETAILED DESCRIPTION

Figure 1:
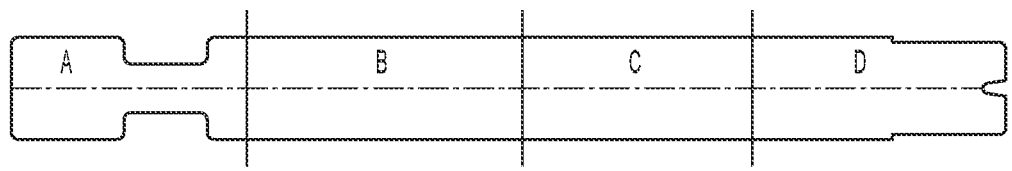
FIG. 1 is a view of a buttress that has been treated in accordance with an embodiment of the present disclosure, showing how the buttress was cut for testing.

Various exemplary embodiments of the present disclosure are discussed herein below in terms of buttresses for use with tissue fixation devices, in embodiments surgical staples. While the below disclosure discusses in detail the use of these buttresses with staples, it will be appreciated that medical devices of the present disclosure include a range of buttressing materials and film-based medical devices that are used to mechanically support tissues, reinforce tissues along staple or suture lines, and decrease the incidence of fluid leakage and/or bleeding of tissues. For example, other suitable medical devices include hernia patches, staples, tacks, stents, and tissue scaffolds.

Medical devices of the present disclosure may be used with any fixation device utilized to close any wound, defect, and/or opening in tissue. Thus, while surgical buttresses are discussed in conjunction with a surgical stapling apparatus, it is envisioned that other fixation devices, such as tacks, sutures, clips, adhesives and the like, may be utilized in conjunction with medical devices of the present disclosure to affix the medical devices to tissue. Medical devices that are not used with a tissue fixation device, or other tissue support devices, are contemplated.

In embodiments, a buttress of the present disclosure may have a therapeutic layer or coating thereon which includes therapeutic agents for further treatment of tissue at or near the site where the surgical buttress of the present disclosure is placed. Thus, the present disclosure describes surgical buttresses, and methods and mechanisms for using the same, for the targeted delivery of therapeutic agents to a patient.

In the following discussion, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is further from the clinician during proper use. As used herein, the term "patient" should be understood as referring to a human subject or other animal, and the term "clinician" should be understood as referring to a doctor, nurse or other care provider and may include support personnel.

Medical devices of the present disclosure, including surgical buttresses, may be fabricated from a biocompatible substrate material which is a bioabsorbable, non-absorbable, natural, or synthetic material. The medical device may also be formed of materials that are porous or non-porous. It should of course be understood that any combination of porous, non-porous, natural, synthetic, bioabsorbable, and/or non-bioabsorbable materials may be used to form a medical device of the present disclosure.

In embodiments, the medical devices of the present disclosure, such as a surgical buttress, may be biodegradable, so that the device does not have to be retrieved from the body. The term "biodegradable" as used herein is defined to include both bioabsorbable and bioresorbable materials. By biodegradable, it is meant that the medical device decomposes or loses structural integrity under body conditions (e.g., enzymatic degradation or hydrolysis), or is broken down (physically or chemically) under physiologic conditions in the body such that the degradation products are excretable or absorbable by the body.

Non-limiting examples of materials which may be used in forming a medical device of the present disclosure, for example a surgical buttress, include, but are not limited to, poly(lactic acid), poly(glycolic acid), poly(trimethylene carbonate), poly(dioxanone), poly(hydroxybutyrate), poly(phosphazine), polyethylene terephthalate, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly(ether-esters), polyalkylene oxalates, polyamides, poly(iminocarbonates), polyalkylene oxalates, polyoxaesters, polyorthoesters, polyphosphazenes, and copolymers, block copolymers, homopolymers, blends and combinations thereof.

In embodiments, natural biological polymers may be used in forming a medical device of the present disclosure. Suitable natural biological polymers include, but are not limited to, collagen, gelatin, fibrin, fibrinogen, elastin, keratin, albumin, cellulose, oxidized cellulose, hydroxyethyl cellulose, hydroxypropyl cellulose, carboxyethyl cellulose, carboxymethyl cellulose, chitin, chitosan, and combinations thereof. In addition, natural biological polymers may be combined with any of the other polymeric materials described herein to produce a medical device of the present disclosure.

In embodiments, a medical device of the present disclosure, such as a surgical buttress, may be formed of porous material(s). Any porous portion of a medical device of the present disclosure may have openings or pores over at least a part of a surface thereof. Suitable porous materials include, but are not limited to, fibrous structures (e.g., knitted structures, woven structures, non-woven structures, etc.) and/or foams (e.g., open or closed cell foams).

In embodiments, the pores may be in sufficient number and size so as to interconnect across the entire thickness of the medical device. Woven fabrics, knitted fabrics and open cell foams are illustrative examples of structures in which the pores can be in sufficient number and size so as to interconnect across the entire thickness of the medical device.

In other embodiments, the pores may not interconnect across the entire thickness of the medical device. Closed cell foams or fused non-woven materials are illustrative examples of structures in which the pores may not interconnect across the entire thickness of the medical device. In some embodiments, pores may be located on a portion of the medical device, with other portions of the medical device having a non-porous texture. Those skilled in the art may envision a variety of pore distribution patterns and configurations for a porous medical device of the present disclosure.

Where the medical device of the present disclosure is porous and includes fibrous materials, the medical device may be formed using any suitable method including, but not limited to, knitting, weaving, non-woven techniques (including melt blowing), wet-spinning, electro-spinning, extrusion, co-extrusion, and the like. In embodiments, the medical device is a surgical buttress possessing a three dimensional structure, such as the textiles described in U.S. Pat. Nos. 7,021,086 and 6,443,964, the entire disclosures of each of which are incorporated by reference herein.

The porosity of the fabric used to form the substrate may allow for the infiltration of biological fluids and/or cellular components which, in turn, may accelerate the release kinetics of any therapeutic agent from the medical device of the present disclosure, thus increasing the rate of release of therapeutic agent(s) from the medical device into the surrounding tissue and fluids.

Substrates used to form medical devices of the present disclosure, such as surgical buttresses, may have a thickness from about 0.05 mm to about 0.5 mm, in embodiments from about 0.1 mm to about 0.2 mm.

Where the substrate used to form the medical device is porous, the medical device of the present disclosure may have a pore volume from about 65% to about 85%, in embodiments from about 70% to about 80%.

As noted above, in embodiments the medical devices of the present disclosure also include therapeutic agent(s) in a therapeutic layer or coating thereon. Therapeutic agents which may be added to a medical device of the present disclosure include, but are not limited to, drugs, amino acids, peptides, polypeptides, proteins, polysaccharides, muteins, immunoglobulins, antibodies, cytokines (e.g., lymphokines, monokines, chemokines), blood clotting factors, hemopoietic factors, interleukins (1 through 18), interferons (β-IFN, α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), hormones and hormone analogs (e.g., growth hormone, luteinizing hormone releasing factor), vaccines (e.g., tumoral, bacterial and viral antigens), somatostatin, antigens, blood coagulation factors, growth factors (e.g., nerve growth factor, insulin-like growth factor), bone morphogenic proteins, TGF-B, protein inhibitors, protein antagonists, protein agonists, nucleic acids, such as antisense molecules, DNA, RNA, RNAi, oligonucleotides, polynucleotides, cells, viruses, and ribozymes.

In embodiments, the therapeutic agent applied to a medical device of the present disclosure may include an antitumor agent and/or tumor suppressor, referred to, in embodiments, as a "chemotherapeutic agent" and/or an "antineoplastic agent." Suitable chemotherapeutic agents include, for example, paclitaxel and derivatives thereof, docetaxel and derivatives thereof, abraxane, tamoxifen, cyclophosphamide, actinomycin, bleomycin, dactinomycin, daunorubicin, doxorubicin, doxorubicin hydrochloride, epirubicin, mitomycin, methotrexate, fluorouracil, gemcitabine, gemcitabine hydrochloride, carboplatin, carmustine (BCNU), methyl-CCNU, cisplatin, etoposide, camptothecin and derivatives thereof, phenesterine, vinblastine, vincristine, goserelin, leuprolide, interferon alfa, retinoic acid (ATRA), nitrogen mustard alkylating agents, piposulfan, vinorelbine, irinotecan, irinotecan hydrochloride, vinblastine, pemetrexed, sorafenib tosylate, everolimus, erlotinib hydrochloride, sunitinib malate, capecitabine oxaliplatin, leucovorin calcium, bevacizumab, cetuximab, ramucirumab, trastuzumab, combinations thereof, and the like.

In embodiments, paclitaxel and/or paclitaxel derivatives may be used as the therapeutic agent. Paclitaxel may have various forms, referred to herein as "polymorphs," including amorphous paclitaxel, crystalline paclitaxel, sometimes referred to as crystalline paclitaxel dihydrate, and/or anhydrous paclitaxel, or mixtures thereof.

In accordance with the present disclosure, the polymorph form of paclitaxel utilized in forming the therapeutic layer may be varied by the aqueous composition, the solvent polarity and the composition of protic and aprotic solvents utilized in the solvent system to form the solution for applying the therapeutic layer. For example, paclitaxel dissolved and then dried from 10% v/v water in methanol will yield a predominantly crystalline paclitaxel dihydrate layer, while the same paclitaxel dissolved and then dried from non-polar solvent dichloromethane will yield a predominantly amorphous layer.

The crystallinity of the paclitaxel will impact its solubility in aqueous systems. Accordingly, the polymorph form of paclitaxel in the therapeutic layer may be adjusted and selected to provide a tailored release of therapeutic agent from the implant of the present disclosure. Although the drug in any form is hydrophobic, as amorphous paclitaxel it is more soluble in aqueous environments, and crystalline paclitaxel is less soluble in aqueous environments, more than one polymorphic form of paclitaxel may be used, in embodiments, to provide implants that have multiple release profiles of paclitaxel. For example, medical devices of the present disclosure having both amorphous paclitaxel and crystalline paclitaxel dihydrate thereon may release a bolus of therapeutic agent upon implantation (in the form of the amorphous paclitaxel), while also slowly releasing the therapeutic agent (in the form of the crystalline paclitaxel dihydrate).

In embodiments with no excipient, the amount of amorphous paclitaxel in the therapeutic layer on the medical device may be from 0% to about 100% by weight of the therapeutic layer, in embodiments from about 10% to about 90% by weight of the therapeutic layer, with the crystalline paclitaxel dihydrate being present in amounts from about 0 to about 100% by weight of the therapeutic layer, in embodiments from about 90% to about 10% by weight of the therapeutic layer.

Medical devices of the present disclosure may release amorphous paclitaxel over a period of time from about 24 hours to about 168 hours, in embodiments from about 48 hours to about 96 hours, and release the crystalline paclitaxel dihydrate over a period of time from about 1 week to about 6 weeks, in embodiments from about 2 weeks to about 4 weeks.

In other embodiments, the therapeutic agent may be applied as part of a coating, including polymeric materials or other carrier components within the purview of those skilled in the art. In embodiments, such coatings may include, for example, degradable coatings such as those prepared from monomers such as glycolide, lactide, trimethylene carbonate, p-dioxanone, epsilon-caprolactone, and combinations thereof. If a coating is utilized, the buttress possessing such a coating should remain supple both during and after implantation.

In other embodiments, regardless of whether the therapeutic agent is applied with or without some additional polymeric material to form a coating, in addition to the therapeutic agents described above, therapeutic layers applied to the substrate material in forming a medical device of the present disclosure may also include excipients to enhance both the ability of the therapeutic agent to adhere to the medical device, in embodiments a surgical buttress, as well as to modify the elution of the therapeutic agent from the medical device.

In embodiments, suitable excipients which may be combined with a therapeutic agent to form the therapeutic layer on the medical device include surfactants such as, but not limited to, cyclodextrins such as 2-hydroxypropyl-beta-cyclodextrin and methyl-ß-cyclodextrin, sodium dodecyl sulfate, octyl glucoside, and sorbitan fatty acid esters such as sorbitan monooleate, sorbitan monolaurate and polyethoxylated fatty acid esters of sorbitan, sometimes referred to herein as polysorbates, including those sold under the name TWEEN™. Examples of such polysorbates include polysorbate 80 (TWEEN™ 80), polysorbate 20 (TWEEN™ 20), polysorbate 60 (TWEEN™ 60), polysorbate 65 (TWEEN™ 65), polysorbate 85 (TWEEN™ 85), combinations thereof, and the like. In embodiments, low molecular weight poly (ethylene glycol)s may be added as an excipient, either alone or in any combination with any of the other above excipients.

In other embodiments, suitable excipients may include salts such as sodium chloride and/or other materials such as urea, oleic acid, citric acid, and ascorbic acid. In yet other embodiments, the excipient may be a stabilizer such as butylated hydroxytoluene (BHT).

Still other suitable excipients include polyhydric alcohols such as D-sorbitol, mannitol, combinations thereof, and the like.

In certain embodiments, suitable excipients include urea, methyl-ß-cyclodextrin, oleic acid, polysorbate 80, D-sorbitol, octylglucoside, combinations thereof, and the like.

In some embodiments, excipients which are hydrotropes may be included in the therapeutic layers of the present disclosure. These materials attract water into the therapeutic layer, which may enhance its degradation and resulting release of the therapeutic agent from the therapeutic layer. However, in view of the high surface to volume ratios for the therapeutic agents in the therapeutic layers of the present disclosure, such excipients are not, in fact, required. Embodiments of the present disclosure include a therapeutic layer having a chemotherapeutic agent without an excipient.

The therapeutic agent(s) and any excipient may be applied to a medical device of the present disclosure by any method within the purview of those skilled in the art. As noted above, in embodiments the therapeutic agent is in a solution, which is then applied to a medical device of the present disclosure, such as a buttress. The solution possessing the therapeutic agent, along with any excipient, may be applied to the medical device by any method within the purview of those skilled in the art, including spraying, dipping, solution casting, combinations thereof, and the like. After application, the solvent may be driven off by methods within the purview of those skilled in the art, including heating, the application of a vacuum, combinations thereof, and the like. Driving off the solvent leaves the therapeutic agent and any excipient behind to form the therapeutic layer on the medical device.

After formation, medical devices of the present disclosure may possess the therapeutic agent in the coated buttress thereon in amounts from about 0.1% to about 50% by weight of the coated buttress, in embodiments from about 1% to about 10% by weight of the coated buttress. While excipients are not required, where present, non-polymeric excipients may be present in an amount from about 0.01% to about 80% by weight of the coated buttress, in embodiments from about 1% to about 11% by weight of the coated buttress. In other embodiments, where present, polymeric excipients may be present in an amount from about 0.014% to about 14% by weight of the coated buttress, in embodiments from about 5% to about 15% by weight of the coated buttress.

After formation, medical devices of the present disclosure may possess the therapeutic agent in the therapeutic layer thereon in amounts from about 0.01% to about 100% by weight of the therapeutic layer, in embodiments from about 1% to about 75% by weight of the therapeutic layer. While excipients are not required, where present, non-polymeric excipients may be present in an amount from about 1% to about 99% by weight of the therapeutic layer, in embodiments from about 8.5% to about 79.4% by weight of the therapeutic layer, and most preferably in embodiments from 9.5% to about 15%. In embodiments, where present, polymeric excipients may be present in an amount from about 1% to about 99% by weight of the therapeutic layer, in embodiments from about 5% to about 15% by weight of the therapeutic layer.

A therapeutic layer having both a therapeutic agent and non-polymeric excipients may have a thickness from about 13 nm to about 2.9 µm, in embodiments from about 25 nm to about 100 nm.

A therapeutic layer having both a therapeutic agent and polymeric excipients may have a thickness from about 2 nm to about 1.1 µm, in embodiments from about 30 nm to about 100 nm.

In other embodiments, the therapeutic layers may include little or no excipients, so very thin therapeutic layers may be applied to the substrate. This will maintain the porosity of the substrate. Such therapeutic layers may have a thickness from about 11 nm to about 218 nm, in embodiments from about 25 nm to about 75 nm.

In embodiments where the substrate is porous, the therapeutic layer may be present on surfaces throughout the substrate, including within the pores itself. Such a device with non-polymeric excipients or no excipients may have the therapeutic layer at a surface to volume ratio from about 500 $mm^{-1}$ to about 90,000 $mm^{-1}$. Such a device with polymeric excipients may have the therapeutic layer at a surface to volume ratio from about 1,100 $mm^{-1}$ to about 87,000 $mm^{-1}$. This high surface to volume ratio enables relatively fast elution of therapeutic agents from the therapeutic layer, especially hydrophobic drugs such as paclitaxel that have low aqueous solubility. A very high surface to area ratio, providing a high surface area for eluding the chemotherapeutic agent, with a low percentage of the weight of the buttress or other device, has been achieved.

In embodiments, the therapeutic layers of the present disclosure may fragment upon affixation of the medical device possessing the therapeutic layer to tissue. This may result in migration of the therapeutic agent to locations distant from the site of implantation, for example in cases where the buttress is attached to the periphery of a lung lobe, therapeutic agent may migrate into mediastinal lymph nodes, while therapeutic agent(s) remaining on the implant may diffuse directly into tissue adjacent the site of implantation.

As described in greater detail in the Examples below, it has surprisingly been found in a dog model that a medical device having paclitaxel in a therapeutic layer of the present disclosure may release paclitaxel throughout the pleural cavity and reach therapeutic levels in other distant sites in the chest cavity, including the chest wall, diaphragm, esophagus, mediastinum, and pericardium. These are all sites of possible local recurrence of cancer after surgical resection. This widespread distribution at therapeutic levels of a poorly soluble drug such as paclitaxel is surprising. Additionally, very low levels of paclitaxel were observed in the blood, meaning toxicity associated with traditional intravenous therapy may be avoided. Utilizing the implants of the present disclosure, a local regional therapy for treating both the lungs and chest is now possible.

Without wishing to be bound by any theory, it is believed multiple mechanisms are responsible for these surprising results. As noted above, the buttress morphology provides a large surface area, giving more opportunity for the paclitaxel to diffuse away from the buttress. Additionally, some of the therapeutic layer flakes off during firing of staples through the medical device, and migrates into the pleural fluid. Once there, the flakes dissolve and deliver paclitaxel wherever the pleural fluid travels. This could explain the distant migration of the paclitaxel to sites like the chest wall, diaphragm, esophagus, and pericardium.

As noted above, the medical device of the present disclosure may be used with any fixation device to further assist in sealing tissue. For example, medical devices of the present disclosure may be used in conjunction with staples, tacks, clips, sutures, adhesives, combinations thereof, and the like.

In embodiments, medical devices of the present disclosure may be used with staples. For example, a surgical buttress formed of a medical device of the present disclosure is provided to reinforce and seal the lines of staples applied to tissue by a surgical stapling apparatus. The buttress may be configured into any shape, size, or dimension suitable to fit any surgical stapling, fastening, or firing apparatus.

In embodiments, the buttresses described herein may be used in sealing a wound by approximating the edges of wound tissue between a staple cartridge and an anvil of a surgical stapling apparatus which contains the buttress. Firing of the surgical stapling apparatus forces the legs of at least one staple to pass through the opening on the staple cartridge and the buttress, the tissue, and the openings on the anvil to secure the buttress to the tissue, to secure the adjoining tissue to one another, and to seal the tissue.

Where the medical device of the present disclosure is used to form a surgical buttress, upon application to a site of bleeding tissue, the buttress may affect hemostasis of said tissue. As used herein, the term "hemostasis" means the arrest of bleeding.

In addition to providing hemostasis at the site of application of the buttress, the medical devices of the present disclosure may also provide for treatment of tissue with the therapeutic agent at both the site of implantation and elsewhere in the body.

In some embodiments, the present disclosure provides methods of treating cancer. These methods include, in embodiments, introducing to a patient needing treatment a surgical stapler having a buttress thereon, the buttress including a coating of a drug, such as a chemotherapeutic agent, and using the stapler to remove an undesired portion of an organ and to place the buttress in a remaining portion of the organ, including stapling the buttress to tissue and cutting the tissue. Where the tissue to be removed is within a patient's body, the method includes introducing the stapler and buttress into the patient's body.

For example, in embodiments, it has been found that for applications such as lung resection in the treatment of lung cancer, the application of medical devices of the present disclosure, in embodiments surgical buttresses, will treat the site of application of the surgical buttress with a chemotherapeutic agent, such as paclitaxel or its derivatives. Moreover, it has been found that the devices of the present disclosure, depending upon the form of the chemotherapeutic agent, excipients, combinations thereof, and the like, may also elute the chemotherapeutic agent therefrom. The chemotherapeutic agent may be physically removed from the surgical buttress by mechanical/physical forces imparted to the buttress upon firing of a staple therethrough. The chemotherapeutic agent may also dissolve into the pleural fluid within the pleural space and travel throughout the space.

In embodiments, the use of the medical devices of the present disclosure, such as surgical buttresses, may be utilized to maintain therapeutic levels of chemotherapeutics such as paclitaxel, thereby continuing to treat a patient and prevent recurrence of non-small cell lung cancer.

Benefits of the introduction of the chemotherapeutic with the medical devices of the present disclosure include, for example:

Eliminates systemic toxicity typically associated with intravenous chemotherapy;

Reduce drug payload to ~10% of conventional intravenous chemotherapy infusion; and Provides prolonged exposure and in the case of paclitaxel provides greater potency at lower drug concentrations.

Several embodiments of the disclosure are described below with reference to the following non-limiting Examples. The Examples are intended to be illustrative only and are not intended to limit the scope of the present disclosure. As used herein, "room temperature" refers to a temperature of from about 20° C. to about 30° C. Also, parts and percentages, such as solution percentages, are by weight unless otherwise indicated.

Example 1

The feasibility of applying paclitaxel to lung staple buttresses was tested as follows. Staple buttresses made of polyglycolic acid were utilized for the tests. Sections of the material were soaked in tetrahydrofuran, chloroform, toluene, dichloromethane or methanol or combinations thereof as potential formulation solvents. The buttresses visually appeared to be compatible with each solvent, with no deformation or tackiness after several days.

The paclitaxel formulation used to coat the buttress material was a solution of 50 mg/mL paclitaxel and 7 mg/mL urea, in 10:90 v/v water:THF (commercially available as FREEPAC™ paclitaxel eluting formulation). The dried formulation was expected to contain a mixture of amorphous paclitaxel and paclitaxel dihydrate). This formulation was used to coat three buttresses.

Roughly 5 mL of the paclitaxel solution described above was placed in three (3) small vials and a buttress (40 mm in length) was delivered to each vial and allowed to soak in the paclitaxel solution for less than 30 seconds. Each buttress was removed with tweezers and allowed to dry. The buttresses appeared visually dry in 15 to 30 seconds after removal from the paclitaxel solution. Each buttress was then placed on a glass plate and allowed to fully dry for about ten minutes.

No real change in the visual appearance of the buttresses was observed. Light handling did not produce any dusting or particulate from the buttresses. Treated and untreated buttresses were photographed at 50× magnification, with little to no difference in the surface appearance observed.

Each buttress and an untreated buttress were analyzed for paclitaxel as follows. Coupons were extracted with 0.5% v/v acetic acid in methanol under sonication for about 30 minutes. The extract was analyzed using an ultrahigh performance liquid chromatograph with UV detection at 229 nm for residual paclitaxel against a standard of known concentration.

Recovery of paclitaxel was observed with a normal related compound profile. No interfering peaks were observed in the untreated buttress. The results are summarized in Table 1 below.

TABLE 1

| | Recovered paclitaxel | | |
|---|---|---|---|
| Sample | Material | Paclitaxel (µg) | % Related Substances |
| 1 | 40 mm buttress | 5362 | 0.16 |
| 2 | 40 mm buttress | 4795 | 0.15 |
| 3 | 40 mm buttress | 5018 | 0.16 |

In view of the above data in Table 1, dip coating appeared to be effective for applying the paclitaxel solution to a buttress.

Example 2

The production of staple buttresses with varying forms of paclitaxel was tested as follows. Paclitaxel solutions were prepared using crystalline paclitaxel dihydrate, amorphous paclitaxel, and a combination of the two (as described above in Example 1). Two of the samples included urea as an excipient.

The formulations prepared, including the amounts and various forms of paclitaxel (PTX), excipient, if any, and the solvents used to make the paclitaxel solutions, are summarized below in Table 2.

TABLE 2

| Sample | PTX (mg/mL) | Urea (mg/mL) | Solvent | PTX polymorph |
|---|---|---|---|---|
| 4 | 50.9 | 7.0 | 90:10 THF:water | mixed di-hydrate:amorphous |
| 5 | 24.9 | 3.5 | 90:10 methanol:water | dihydrate |

TABLE 2-continued

| Sample | PTX (mg/mL) | Urea (mg/mL) | Solvent | PTX polymorph |
|---|---|---|---|---|
| 6 | 25.6 | 0.0 | methylene chloride | amorphous |

Sample 4 included urea as an excipient. For consistency, urea was included at the same ratio in the dihydrate material (sample 5). No urea was included in the amorphous formulation (sample 6).

90×10 mm buttress profiles (8 cm² one-sided fabric area) were dip coated in each formulation and dried. As with the results described above in Example 1, there was no visible change to the surface of the buttress with any of the formulations. The drug showed excellent affinity to the polymer fabric and a buttress from each formulation was aggressively handled, shaken, and hit against a glass plate with no visible shedding of drug. The coated buttresses were set aside for elution analysis.

Example 3

A formulation of paclitaxel in 10:90 v/v toluene:THF was prepared at a concentration of 51.1 mg/mL, and designated Sample 8. This formulation produces an amorphous paclitaxel layer, which was used to coat five 90×10 mm buttress profiles (8 cm² one-sided fabric area)(referred to as Samples 8.1, 8.2, 8.3, 8.4 and 8.5), each of which was weighed prior to application. After application, each buttress was cut into four pieces, A, B, C, and D, as depicted in FIG. 1. Each section was weighed and then tested per a developmental drug content method. Buttresses were extracted with 0.5% v/v acetic acid in methanol under sonication for 15 minutes. The sample extracts were analyzed using a UPLC with UV detection at 229 nm for both paclitaxel and related compounds against a standard of known paclitaxel concentration using a water and acetonitrile gradient on an Agilent Zorbax RRHD Eclipse PlusC18, 2.1×100 mm, 1.8-µm particle size column.

Weights, drug mass, and % weight/weight observed on each segment of the buttress is summarized below in Tables 3, 4 and 5.

TABLE 3

| Sample | Uncoated Weight (mg) | Coated Weights (mg) by segment | | | | | Delta (mg) | % weight gain |
|---|---|---|---|---|---|---|---|---|
| | | A | B | C | D | Total | | |
| 8.1 | 41.18 | 14.06 | 9.57 | 10.99 | 10.5 | 45.12 | 3.94 | 9.57 |
| 8.2 | 42.71 | 12.5 | 13.04 | 9.77 | 11.33 | 46.64 | 3.93 | 9.20 |
| 8.3 | 43.53 | 13.42 | 12.38 | 9.11 | 12.72 | 47.63 | 4.10 | 9.42 |
| 8.4 | 43.32 | 11.44 | 13.11 | 11.33 | 11.05 | 46.93 | 3.61 | 8.33 |
| 8.5 | 42.22 | 12.22 | 13.4 | 10.98 | 9.82 | 46.42 | 4.20 | 9.95 |

TABLE 4

| | Recovered paclitaxel (mg) per segment | | | | |
|---|---|---|---|---|---|
| | A | B | C | D | Total |
| 8.1 | 1.35 | 0.90 | 1.02 | 0.82 | 4.08 |
| 8.2 | 1.14 | 1.10 | 0.84 | 0.90 | 3.97 |
| 8.3 | 1.33 | 1.15 | 0.79 | 1.05 | 4.33 |
| 8.4 | 1.07 | 1.13 | 0.95 | 0.85 | 4.00 |
| 8.5 | 1.14 | 1.14 | 0.91 | 0.84 | 4.03 |

TABLE 5

| | Paclitaxel, % weight/weight per segment | | | | |
|---|---|---|---|---|---|
| Sample | A | B | C | D | Avg |
| 8.1 | 9.57 | 9.41 | 9.25 | 7.84 | 9.02 |
| 8.2 | 9.10 | 8.43 | 8.62 | 7.91 | 8.51 |
| 8.3 | 9.94 | 9.31 | 8.64 | 8.28 | 9.04 |
| 8.4 | 9.36 | 8.65 | 8.35 | 7.65 | 8.50 |
| 8.5 | 9.32 | 8.53 | 8.28 | 8.56 | 8.67 |

As can be seen from the data summarized in Table 3 above, the buttress material gained 9.3% weight on average, or about 4 mg of drug. Results of recovered paclitaxel (Table 4) and paclitaxel observed as % weight/weight per segment (Table 5) were fairly consistent.

Example 4

Sheets of polyglycolic acid fabric were punched to form 90×10 mm buttress profiles, and then paclitaxel formulations were applied thereto. The formulations and testing are described below.

Paclitaxel formulations were prepared at concentrations of 25 mg/mL with various excipients. Crystallinity of the paclitaxel in samples 10, 11 and 12 was controlled for, with the paclitaxel being either completely crystalline paclitaxel dihydrate or a fully amorphous form. The composition of the remaining samples (9, 13, 14, 15 and 16), based on the 10:90 water:THF solvent system described above in Example 1, is expected to contain a mixture of amorphous paclitaxel and paclitaxel dihydrate. The various formulations are summarized below in Table 6.

TABLE 6

| Sample | Paclitaxel (PTX) polymorph | Solvent | (PTX) (mg/mL) | Excipient (Exc) | Exc (mg/mL) | PTX:Exc (mol:mol) |
|---|---|---|---|---|---|---|
| 9 | PTX semi crystalline w/Urea | 10% water in THF | 24.99 | Urea | 3.50 | 1:2 |

TABLE 6-continued

| Sample | Paclitaxel (PTX) polymorph | Solvent | (PTX) (mg/mL) | Excipient (Exc) | Exc (mg/mL) | PTX:Exc (mol:mol) |
|---|---|---|---|---|---|---|
| 10 | PTX Dihydrate w/Urea | 10% water in 65:35 v:v MeOH:acetone | 24.83 | Urea | 3.50 | 1:2 |
| 11 | PTX Dihydrate | 10% water in 65:35 v:v MeOH:acetone | 25.17 | NA | NA | NA |
| 12 | Amorphous PTX | 10% toluene in THF | 25.00 | NA | NA | NA |
| 13 | PTX semi crystalline | 10% water in THF | 24.86 | Methyl-β-Cyclodextrin | 76.59 | 1:2 |
| 14 | PTX semi crystalline | THF w/1.3% water, 2.9% EtOH | 25.13 | Oleic Acid/ Na Oleate | 3.1 | 1:0.37 |
| 15 | PTX semi crystalline | 10% water in THF | 24.89 | Tween 80/ Sorbitol | 0.375/21.62 | 1:0.01/1:4 |
| 16 | PTX semi crystalline | 10% water in THF | 25.16 | Octylglucoside | 34.37 | 1:4 |

Five milliliters of each of the above formulations was prepared and poured into the reservoir of a coating fixture (the reservoir volume was 25 mL). A sheet of twelve buttress profiles was passed through the reservoir by hand, coating the material, and was held with tweezers to dry. All solvent systems dried very quickly, within less than 30 seconds.

As in earlier Examples 1 and 2 above, little to no change was visible on the material to the naked eye for all formulations, with the exception of sample 10 (crystalline paclitaxel dihydrate with urea). For that sample, some white streaking and non-uniform coating was observed. Buttress profiles were removed from the sheet with tweezers.

The buttresses were then tested for drug potency/uniformity. Five buttresses from each formulation (designated sample 9-1, 9-2, 9-3, 9-4, 9-5, 10-1, 10-2, 10-3, etc.) were extracted and tested per a developmental drug content method. Buttresses were extracted with 0.5% v/v acetic acid in methanol under sonication for 15 minutes. The sample extracts were analyzed using a UPLC with UV detection at 229 nm for both paclitaxel and related compounds against a standard of known paclitaxel concentration using a water and acetonitrile gradient on an Agilent Zorbax RRHD Eclipse PlusC18, 2.1×100 mm, 1.8-μm particle size column.

Figure 2:
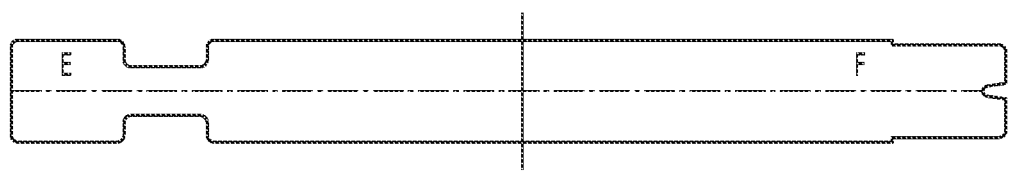
FIG. 2 is an alternate view of a buttress that has been treated in accordance with an embodiment of the present disclosure, showing a different pattern for cutting the buttress for testing.

Each buttress was cut into two segments, E and F, as depicted in FIG. 2. The segments, representing roughly half of the buttress profile, were weighed and tested individually.

Figure 3:
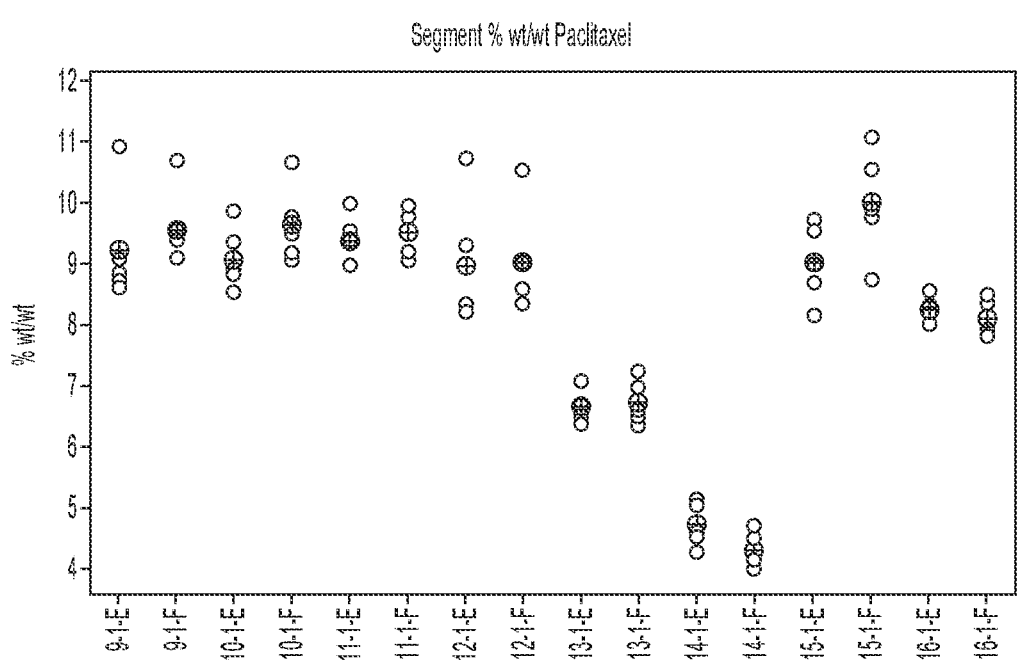
FIG. 3 is a graph showing the % weight/weight paclitaxel found on the individual segments of buttress as depicted in FIG. 2 after application of paclitaxel thereto.

The segment and total values are shown in FIG. 3 (FIG. 3 has % weight/weight paclitaxel for the individual segments) and Table 7 below (the letter for each sample corresponding with the segment tested as depicted in FIG. 2), and the averages for each formulation are shown below in Table 8 below.

TABLE 7

| Individual segments % weight/weight paclitaxel | | | |
|---|---|---|---|
| Sample | Weight (mg) | Paclitaxel (μg) | Paclitaxel % weight/weight |
| 9-1-E | 20.93 | 1808 | 8.64 |
| 9-1-F | 17.70 | 1611 | 9.10 |
| 9-2-E | 21.83 | 1985 | 9.09 |
| 9-2-F | 23.06 | 2096 | 9.09 |
| 9-3-E | 18.29 | 1999 | 10.93 |
| 9-3-F | 21.73 | 2327 | 10.71 |
| 9-4-E | 20.23 | 1772 | 8.76 |
| 9-4-F | 22.81 | 2180 | 9.56 |
| 9-5-E | 18.40 | 1628 | 8.85 |
| 9-5-F | 18.68 | 1757 | 9.41 |
| 10-1-E | 18.33 | 1624 | 8.86 |
| 10-1-F | 19.97 | 1896 | 9.49 |
| 10-2-E | 21.95 | 1872 | 8.53 |
| 10-2-F | 21.65 | 1963 | 9.07 |
| 10-3-E | 17.69 | 1657 | 9.37 |
| 10-3-F | 20.13 | 1970 | 9.79 |
| 10-4-E | 17.46 | 1724 | 9.87 |
| 10-4-F | 20.11 | 2148 | 10.68 |
| 10-5-E | 21.56 | 1923 | 8.92 |
| 10-5-F | 21.35 | 1963 | 9.19 |
| 11-1-E | 16.26 | 1460 | 8.98 |
| 11-1-F | 19.60 | 1777 | 9.07 |
| 11-2-E | 20.71 | 1976 | 9.54 |
| 11-2-F | 22.35 | 2185 | 9.78 |
| 11-3-E | 19.78 | 1858 | 9.39 |
| 11-3-F | 21.59 | 2073 | 9.60 |
| 11-4-E | 20.35 | 1834 | 9.01 |
| 11-4-F | 17.63 | 1623 | 9.21 |
| 11-5-E | 20.09 | 2008 | 10.00 |
| 11-5-F | 19.01 | 1895 | 9.97 |
| 12-1-E | 16.16 | 1504 | 9.31 |
| 12-1-F | 18.41 | 1584 | 8.60 |
| 12-2-E | 20.04 | 2150 | 10.73 |
| 12-2-F | 17.88 | 1886 | 10.55 |
| 12-3-E | 15.74 | 1293 | 8.21 |
| 12-3-F | 18.89 | 1622 | 8.59 |
| 12-4-E | 17.15 | 1422 | 8.29 |
| 12-4-F | 20.48 | 1718 | 8.39 |
| 12-5-E | 22.15 | 1851 | 8.36 |
| 12-5-F | 20.51 | 1857 | 9.05 |
| 13-1-E | 24.37 | 1592 | 6.53 |
| 13-1-F | 26.71 | 1768 | 6.62 |
| 13-2-E | 22.95 | 1626 | 7.08 |
| 13-2-F | 21.79 | 1583 | 7.26 |
| 13-3-E | 19.45 | 1290 | 6.63 |
| 13-3-F | 26.46 | 1685 | 6.37 |
| 13-4-E | 21.00 | 1344 | 6.40 |
| 13-4-F | 22.63 | 1468 | 6.49 |
| 13-5-E | 25.79 | 1732 | 6.72 |
| 13-5-F | 19.90 | 1393 | 7.00 |
| 14-1-E | 20.31 | 872 | 4.29 |
| 14-1-F | 25.54 | 1020 | 3.99 |
| 14-2-E | 22.78 | 1031 | 4.53 |
| 14-2-F | 24.94 | 1027 | 4.12 |
| 14-3-E | 22.51 | 1038 | 4.61 |

TABLE 7-continued

Individual segments % weight/weight paclitaxel

| Sample | Weight (mg) | Paclitaxel (µg) | Paclitaxel % weight/weight |
|---|---|---|---|
| 14-3-F | 25.35 | 1065 | 4.20 |
| 14-4-E | 20.30 | 1030 | 5.07 |
| 14-4-F | 27.83 | 1258 | 4.52 |
| 14-5-E | 26.34 | 1360 | 5.16 |
| 14-5-F | 25.18 | 1184 | 4.70 |
| 15-1-E | 20.67 | 1797 | 8.69 |
| 15-1-F | 17.99 | 1899 | 10.56 |
| 15-2-E | 17.93 | 1745 | 9.73 |
| 15-2-F | 20.18 | 1770 | 8.77 |
| 15-3-E | 19.59 | 1766 | 9.01 |
| 15-3-F | 16.89 | 1672 | 9.90 |
| 15-4-E | 22.66 | 1852 | 8.17 |
| 15-4-F | 19.91 | 1946 | 9.77 |
| 15-5-E | 18.43 | 1763 | 9.57 |
| 15-5-F | 20.86 | 2314 | 11.09 |
| 16-1-E | 20.37 | 1639 | 8.05 |
| 16-1-F | 18.93 | 1609 | 8.50 |
| 16-2-E | 20.23 | 1644 | 8.13 |
| 16-2-F | 20.31 | 1587 | 7.81 |
| 16-3-E | 17.59 | 1464 | 8.32 |
| 16-3-F | 22.21 | 1758 | 7.92 |
| 16-4-E | 18.30 | 1507 | 8.23 |
| 16-4-F | 20.06 | 1579 | 7.87 |
| 16-5-E | 19.11 | 1639 | 8.58 |
| 16-5-F | 23.03 | 1923 | 8.35 |

TABLE 8

Average potency values ± SD

| Formulation | Weight (mg) | Paclitaxel (µg) | Paclitaxel % weight/weight |
|---|---|---|---|
| 9 | 40.73 ± 3.20 | 3833 ± 416 | 9.41 ± 0.79 |
| 10 | 40.04 ± 2.96 | 3748 ± 165 | 9.39 ± 0.59 |
| 11 | 39.47 ± 2.82 | 3738 ± 379 | 9.46 ± 0.40 |
| 12 | 37.48 ± 3.30 | 3377 ± 474 | 9.01 ± 0.94 |
| 13 | 46.21 ± 2.87 | 3096 ± 211 | 6.70 ± 0.30 |
| 14 | 48.22 ± 2.06 | 2177 ± 249 | 4.50 ± 0.33 |
| 15 | 39.02 ± 2.24 | 3705 ± 252 | 9.50 ± 0.55 |
| 16 | 40.03 ± 1.42 | 3270 ± 176 | 8.17 ± 0.19 |

As can be seen from the data in Tables 7 and 8, there was a fair amount of variation in the individual buttress weights, but the % weight/weight of paclitaxel in the therapeutic layers was fairly consistent within each group. Most formulations had between 8 and 10% drug by weight. Formulations 13 (methyl-ß-cyclodextrin excipient) and 14 (oleic acid/Na oleate excipient) had less drug in the therapeutic layer.

Figure 4:
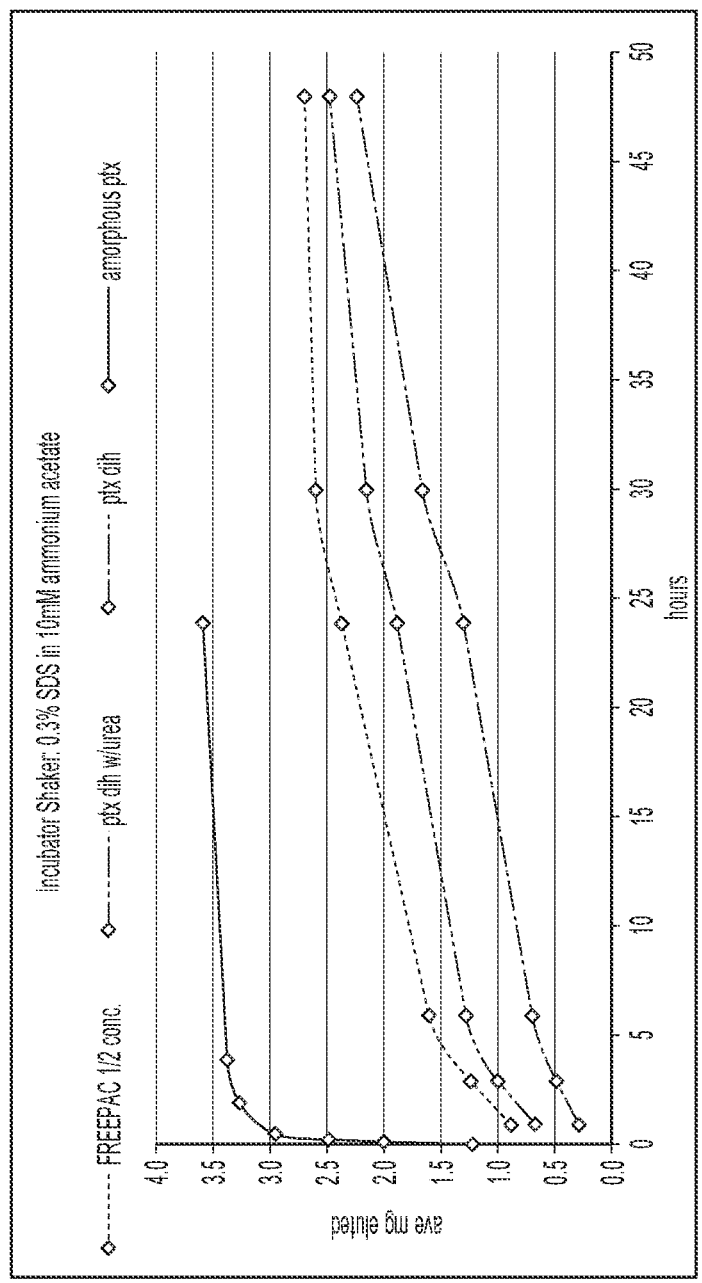
FIG. 4 is a graph showing the average cumulative paclitaxel eluted from buttresses with various coatings.

Drug elution from the buttresses was then examined as follows. Three buttresses from each formulation were mounted on mandrels and introduced to 37° C. 0.3% SDS in 10 mM ammonium acetate and placed in a 37° C. incubator shaker at 100 rpm. At each timepoint, the mandrel and buttress were removed and transferred to a fresh vial of media. Timepoints varied per formulation. An aliquot of each formulation was filtered through a 0.2 µm nylon filter and analyzed by a developmental HPLC method for similar sample types. A water and acetonitrile gradient on a Luna 3 µm PFP(2) 100 Å, 4.6×100 column was used for separation with UV detection at 229 nm against a standard of known paclitaxel concentration. FIG. 4 is a graph showing the average cumulative drug eluted from the buttresses. Tables 9, 10, 11, and 12 below summarize the cumulative drug eluted for the buttresses of Formulations 9, 10, 11 and 12, respectively.

TABLE 9

Formulation 9 cumulative drug eluted (µg)

| Time (min) | 60 | 180 | 360 | 1440 | 1800 | 2880 |
|---|---|---|---|---|---|---|
| Buttress 1 | 843 | 1202 | 1585 | 2358 | 2511 | 2530 |
| Buttress 2 | 834 | 1168 | 1510 | 2290 | 2505 | 2639 |
| Buttress 3 | 1012 | 1369 | 1722 | 2495 | 2790 | 2958 |
| Avg | 896 | 1246 | 1606 | 2381 | 2602 | 2709 |
| SD | 100 | 108 | 108 | 104 | 163 | 222 |
| % RSD | 11 | 9 | 7 | 4 | 6 | 8 |

TABLE 10

Formulation 10 cumulative drug eluted (µg)

| Time (min) | 60 | 180 | 360 | 1440 | 1800 | 2880 |
|---|---|---|---|---|---|---|
| Buttress 1 | 699 | 1044 | 1324 | 1916 | 2165 | 2408 |
| Buttress 2 | 673 | 1023 | 1357 | 1979 | 2297 | 2627 |
| Buttress 3 | 661 | 928 | 1195 | 1765 | 2009 | 2416 |
| Avg | 678 | 998 | 1292 | 1887 | 2157 | 2484 |
| SD | 20 | 62 | 86 | 110 | 144 | 124 |
| % RSD | 3 | 6 | 7 | 6 | 7 | 5 |

TABLE 11

Formulation 11 cumulative drug eluted (µg)

| Time (min) | 60 | 180 | 360 | 1440 | 1800 | 2880 |
|---|---|---|---|---|---|---|
| Buttress 1 | 288 | 459 | 652 | 1254 | 1569 | 2143 |
| Buttress 2 | 322 | 527 | 757 | 1343 | 1706 | 2282 |
| Buttress 3 | 288 | 482 | 710 | 1332 | 1712 | 2290 |
| Avg | 299 | 489 | 707 | 1310 | 1662 | 2239 |
| SD | 20 | 35 | 53 | 48 | 81 | 83 |
| % RSD | 7 | 7 | 7 | 4 | 5 | 4 |

TABLE 12

Formulation 12 cumulative drug eluted (µg)

| Time (min) | 5 | 10 | 15 | 30 | 120 | 240 | 1440 |
|---|---|---|---|---|---|---|---|
| Buttress 1 | 1096 | 1668 | 1979 | 2317 | 2531 | 2582 | 2707 |
| Buttress 2 | 1356 | 2401 | 3053 | 3657 | 4082 | 4218 | 4542 |
| Buttress 3 | 1225 | 1988 | 2437 | 2925 | 3252 | 3345 | 3559 |
| Avg | 1225 | 2019 | 2489 | 2966 | 3289 | 3382 | 3603 |
| SD | 130 | 367 | 539 | 671 | 776 | 818 | 919 |
| % RSD | 11 | 18 | 22 | 23 | 24 | 24 | 25 |

As can be seen from the data set forth in Tables 9-12, by varying the excipients and forms of paclitaxel applied to a buttress, as well as the solvents used to form the solutions used to apply the paclitaxel and excipient to the buttress, both the amounts of paclitaxel released from the buttresses and the release profiles of the paclitaxel (e.g., bolus vs. extended release) could be adjusted.

Figure 6:
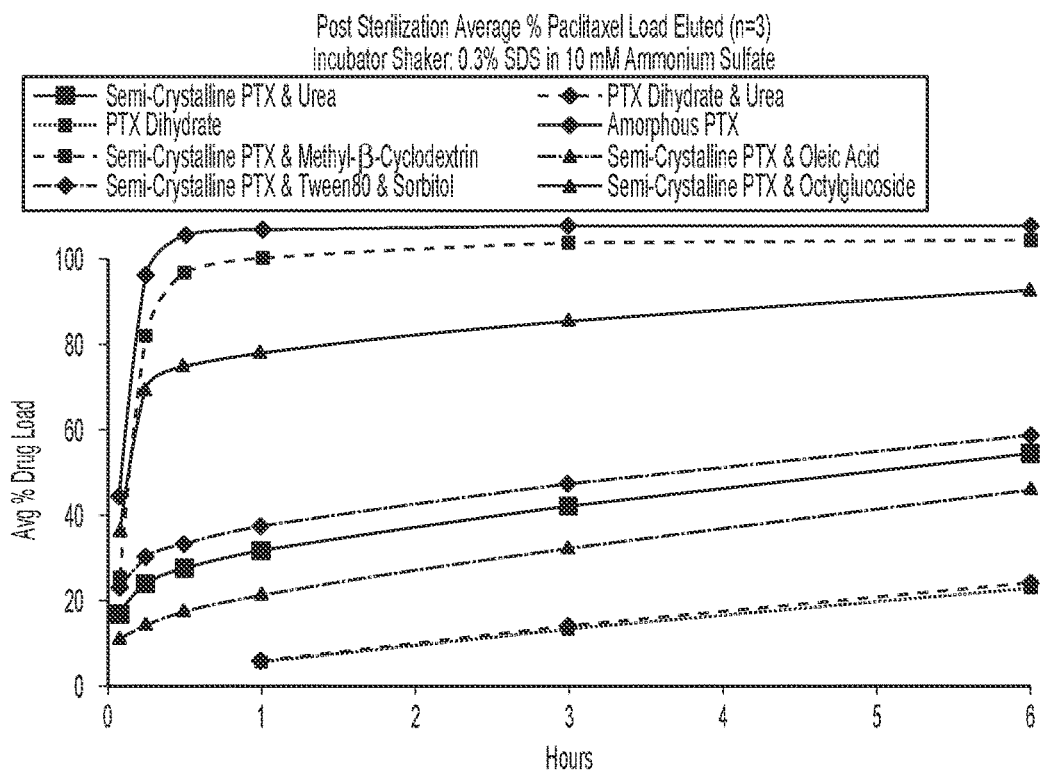
FIG. 6 is a graph depicting the elution curves for formulations 9-16 of the present disclosure.

FIG. 6 is a graph depicting the elution curves for formulations 9-16.

The surface of each buttress was imaged by a scanning electron microscope (SEM). Results were generally as expected, with crystalline formulations showing needle formations, and amorphous formulations showing tightly coated fibers and some webbing between fibers. Formulation 16 differed slightly in that it appeared to more thoroughly coat the material than the other semi-amorphous formulations.

Example 5

A study was conducted where buttresses of the present disclosure were implanted in the pleural cavity of dogs, and the elution and migration of drug on the buttress was measured.

Briefly, two formulations were implanted in a total of four dogs (one formulation in two dogs and the other formulation in the other two dogs). Bilateral thoracotomies were created and 60 mm staplers having two of the buttresses with paclitaxel thereon were utilized. The first buttress included the formulation of Example 5, sample 9 (semi-crystalline paclitaxel and urea) and the second buttress was the amorphous paclitaxel described above in Example 5, sample 12. The two dogs having the first buttress were referred to as FREEPAC #1 (or PTX+urea dog #1) and FREEPAC #2 (or PTX+urea dog #1), and the two dogs having the second buttress were referred to as Amorph dog #1 and Amorph dog #2.

Each buttress was fired across the tips of five or six lung lobes for each animal. A mediastinum fenestration was placed to allow liquid and air communication between hemi-thoraces. A chest drain was placed and both thoracotomies were closed. The chest drains were removed within about 36 to about 48 hours after surgery. The four animals were euthanized 7 days after surgery and tissues of interest were collected for paclitaxel analysis. The tissues collected included: 1) tissue at the buttress staple line; 2) tissue adjacent the staple line; and 3) various locations away from the buttress, including the thoracic wall, mediastinum, heart, pericardium, mediastinal lymph nodes, remnant lobes, esophagus, bronchus, and diaphragm.

The plasma levels of paclitaxel, and the paclitaxel levels in the chest drain fluid compared with implant time, were also tracked for each animal. Plasma was collected intra-operatively, and then post-operatively at 30 minutes, 1 hour, 2 hours, 4 hours, 6 hours, 24 hours, 72 hours, and 168 hours.

At necropsy, each of the tissues being sampled was divided into a 3×3 cm grid and then further sliced into three layers to produce 27 samples for paclitaxel drug analysis. The lung sectioning scheme for the tissue adjacent the buttress is outlined in FIG. 5.

Figure 7:
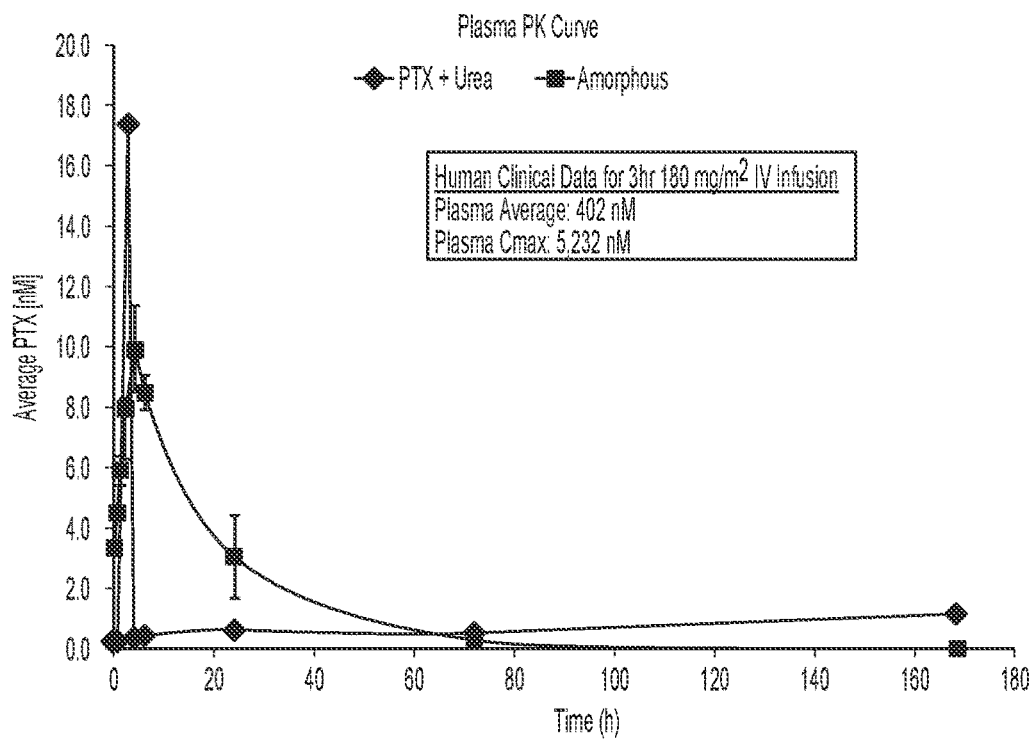
FIG. 7 is a graph depicting plasma levels of paclitaxel after placement of two buttresses of the present disclosure in a dog.

Graphs summarizing the results obtained are set forth as FIGS. 7-10. As depicted in FIG. 7, the plasma levels of both the buttress with amorphous paclitaxel and the buttress with the combination of amorphous paclitaxel and paclitaxel dihydrate with urea subsided over time, with low plasma levels. (The inset box in FIG. 7 is taken from human clinical data (Ohtsu et al.) for a 180 mg/m$^2$ infusion administered over a 3-hour period. The reported average Cmax value for 3 patients was 5,232±151 nM, while the average plasma value for 3 patients was 402±3 nM, assuming a clearance period of 48 hours to reach paclitaxel plasma levels below therapeutic levels of 30 nM. Local delivery of paclitaxel at the site of lung tissue resection resulted in minimal delivery of drug to the plasma. In fact, both formulations did not cross the therapeutic threshold, with peak levels more than two orders of magnitude lower than normally experienced after a clinical intravenous (IV) dose of paclitaxel. It should also be noted that none of the four dogs experienced any signs of drug toxicity typically experienced with IV paclitaxel delivery, including no significant change in bloodstream neutrophil cell count.)

Figure 8:
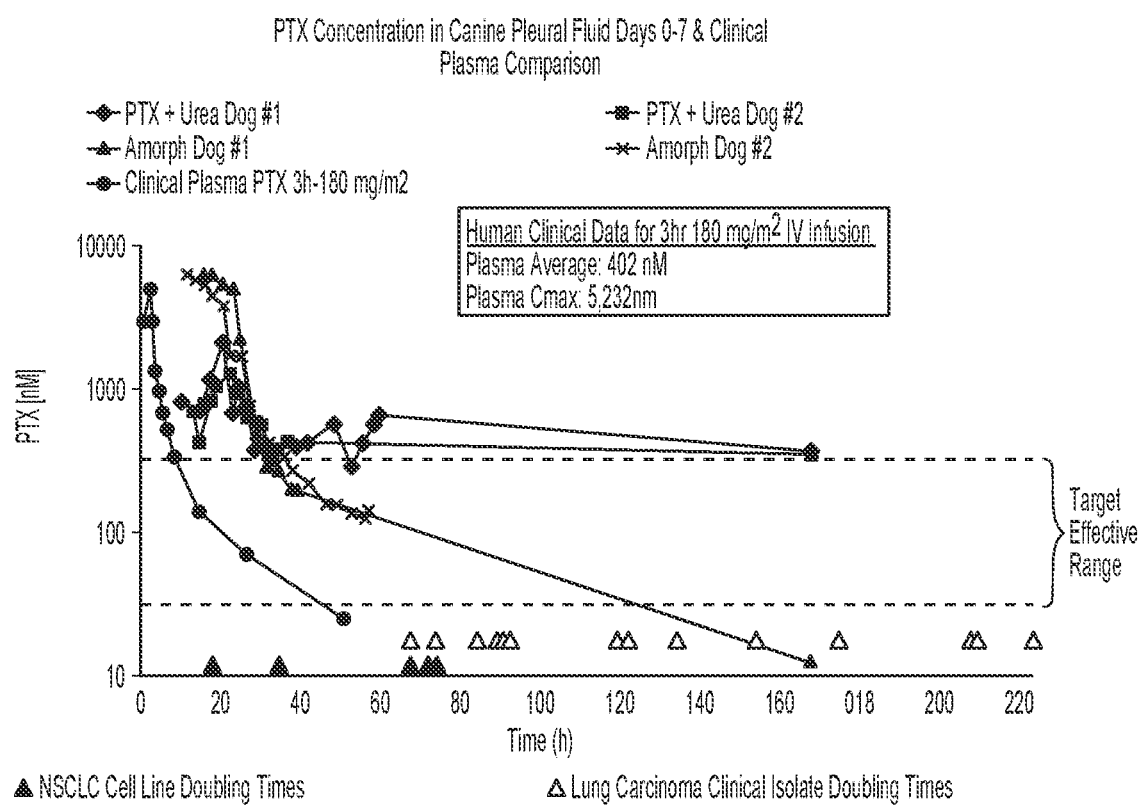
FIG. 8 is a graph summarizing the paclitaxel concentration in canine pleural fluid for days 0-7 after implantation, compared with observed clinical plasma levels.

FIG. 8 summarizes the paclitaxel concentration in canine pleural fluid for days 0-7 after implantation, compared with observed clinical plasma levels. As set forth in FIG. 8, paclitaxel (PTX) pleural fluid concentration in canine study was compared with overlaid clinical plasma paclitaxel levels (Filled circles) and overlaid NSCLC cell line doubling times (Filled triangles) and lung carcinoma clinical isolate doubling times (Open triangles). Target paclitaxel effective range is highlighted in area bordered by dashed lines. The target therapeutic range was determined by adjusting experimental in vitro NSCLC cell line IC90 values with a factor to account for the impact of the in vivo tumor environment. Two paclitaxel containing formulations (semicrystalline paclitaxel+urea vs. amorphous paclitaxel) were each implanted into the lungs of canines for seven days. Plasma and pleural fluid paclitaxel levels were monitored at several time points and paclitaxel tissue levels were measured at seven days post-surgery. The semicrystalline paclitaxel+urea formulation sustained therapeutic levels of paclitaxel in the pleural fluid up to at least the 7 day study termination time point, whereas the amorphous formulation maintained therapeutic levels up to at least 40-60 hours, at which point chest drains were removed. Both locally delivered formulations sustained therapeutic levels of paclitaxel in the pleural fluid space longer than achieved in plasma after intravenous injection in humans. Additionally, both local formulations sustained therapeutic levels beyond the cell doubling times of many lung carcinoma clinical isolates, indicating improved chance of efficacy compared to intravenous paclitaxel administration.

The inset box in FIG. 8 is taken from human clinical data (Ohtsu et al.) for a 180 mg/m$^2$ infusion administered over a 3-hour period. The reported average Cmax value for 3 patients was 5,232±151 nM, while the average plasma value for 3 patients was 402±3 nM, assuming a clearance period of 48 hours to reach paclitaxel plasma levels below 30 nM. The clinical paclitaxel plasma levels reported by Ohtsu for a 180 mg/m$^2$ infusion administered over a 3-hour period is plotted in comparison to the paclitaxel pleural fluid levels found in the 7-day canine study. It has been demonstrated in multiple preclinical models that paclitaxel levels in tissues follow plasma levels after IV injection (See, Eiseman, et al. Cancer Chemother. Pharmacol. 1994; 34(6):465-71; Soma, et al. J. Surg. Res. 2009 July; 155(1):142-6; Schrump, et al. J. Thorac. Cardiovasc. Surg. 2002 April; 123(4):686-94.)

Paclitaxel levels in lung after IV injection in mice, rabbits, and sheep are within 0.6-4.3 times the levels found in plasma on a drug mass/tissue mass basis up until plasma levels begin to approach sub-therapeutic paclitaxel levels. Importantly, when paclitaxel is cleared from the bloodstream it is also rapidly washed out of lung and other tissues. From these preclinical observations it can be inferred that IV paclitaxel administered to humans remains at therapeutic concentrations in lung tissue not much longer than 48 hours after initiation of treatment.

It has also been demonstrated that paclitaxel potency increases with exposure time and is more effective at lower concentrations against faster dividing cell types. This effect of increasing potency with exposure duration can be attributed to paclitaxel's mechanism of action; namely paclitaxel must be at sufficiently high concentrations during cell division to disrupt microtubule polymerization and thus cause cell death. Because of this effect, paclitaxel is most effective as a chemotherapeutic agent against slowly dividing cancer cells when maintained over a long period of time at therapeutic levels in the tissue of interest. For example, it has been demonstrated that primary lung carcinoma tumors collected as clinical isolates from 15 affected patients had doubling times ranging from approximately 68 to 296 hours. (Baguley, et al., "Inhibition of growth of primary human tumour cell cultures by a 4-anilinoquinazoline inhibitor of the epidermal growth factor receptor family of tyrosine kinases," Eur. J. Cancer. 1998 June; 34(7):1086-90.)

Because sustained localized delivery of paclitaxel enables therapeutic levels for much longer periods than intravenous therapy this mode of delivery should provide superior efficacy against NSCLC.

Figure 9:
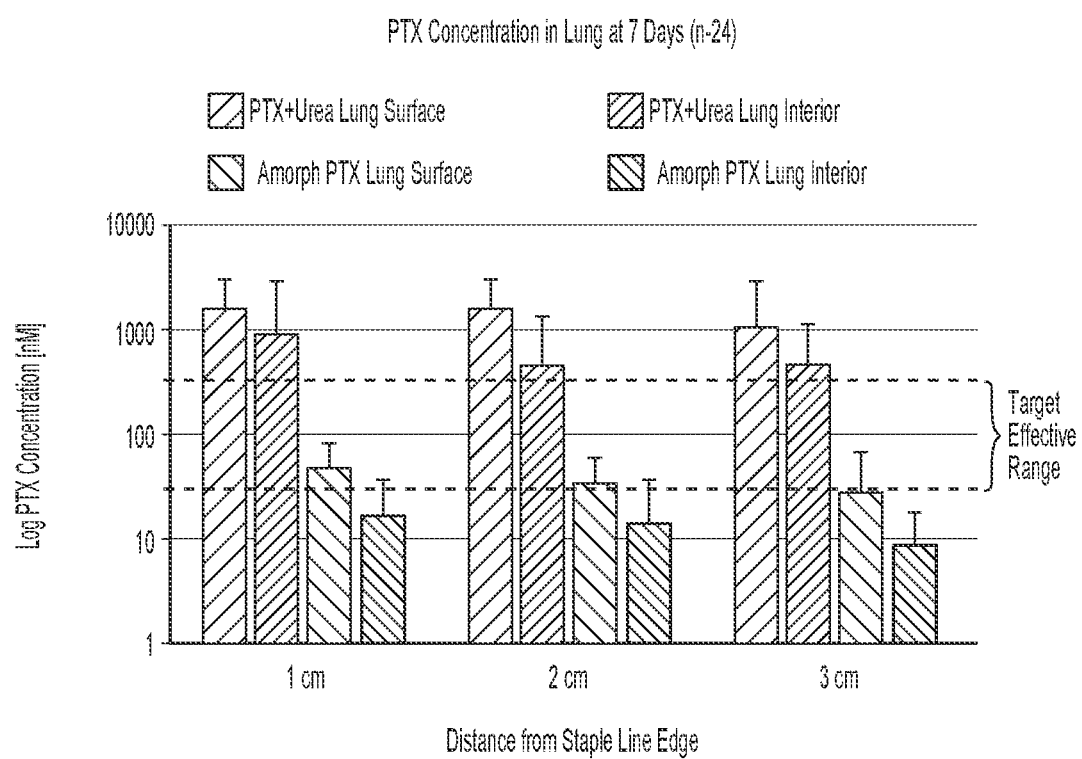
FIG. 9 is a graph showing the concentration of various paclitaxel formulations of the present disclosure in the dog lung after 7 days, with varying distances from the staple line.

FIG. 9 is a graph summarizing the concentration of various paclitaxel formulations in the lung after 7 days, with varying distances from the staple line. Therapeutic levels of paclitaxel were found in canine lung both on the surface and in the lung interior up to 3 cm away from the staple line buttress edge at 7 days post-surgery for the semicrystalline paclitaxel+urea formulation. The amorphous paclitaxel formulation produced therapeutic levels at the surface of lung but not in the lung interior.

Figure 10:
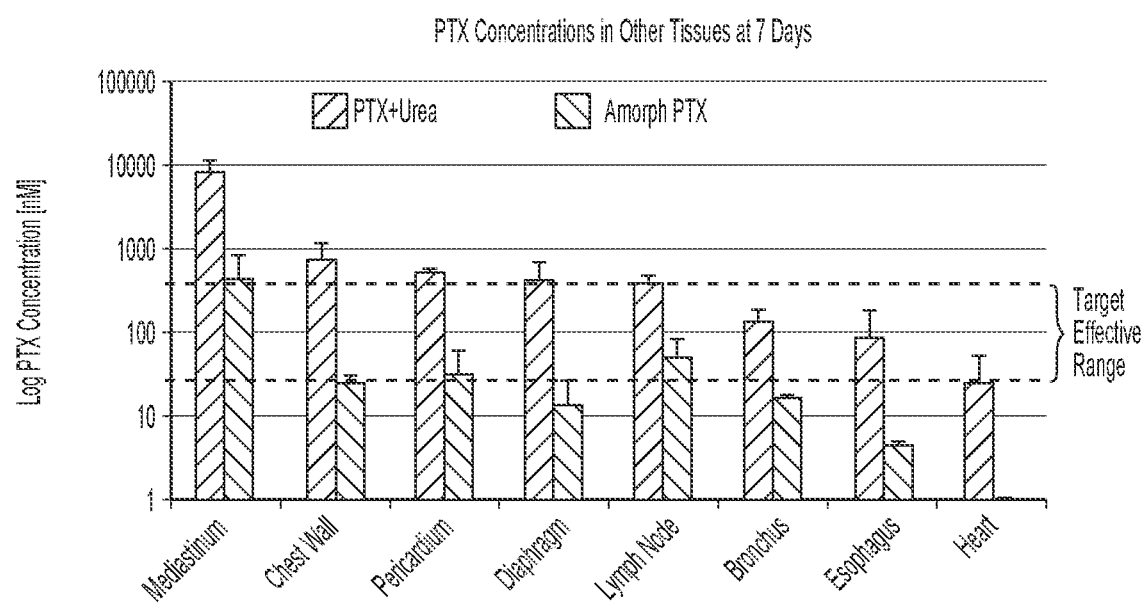
FIG. 10 is a graph showing paclitaxel concentrations of paclitaxel formulations in other tissues (mediastinum, chest wall, pericardium, diaphragm, mediastinal lymph node, bronchus, esophagus and heart) after 7 days.

FIG. 10 is a graph summarizing paclitaxel concentrations of various paclitaxel formulations in other tissues (mediastinum, chest wall, pericardium, diaphragm, lymph node, bronchus, esophagus and heart) after 7 days. At 7 days post-surgery the semicrystalline paclitaxel+urea formulation produced therapeutic levels of paclitaxel in all regional tissues sampled in the ipsilateral chest except for the heart, whereas the amorphous paclitaxel formulation produced therapeutic levels in the mediastinum and mediastinal lymph node. The distant delivery of therapeutic levels of paclitaxel to the mediastinum and mediastinal lymph nodes is significant as these are sites of typical local and regional recurrence after lobectomies and sublobar resections respectively. In theory, paclitaxel delivery to these structures should reduce the risk of locoregional recurrence after surgery for early stage NSCLC. Additionally, delivery of therapeutic levels of paclitaxel to the chest wall, diaphragm, bronchus and esophagus should reduce the risk of recurrence in these structures as well.

In addition, therapeutic levels of paclitaxel were found in mediastinal lymph nodes after implantation of the implants of the present disclosure. The nodes in which the paclitaxel was found were several centimeters away from the buttressed staple lines. The concentrations of paclitaxel in the lymph node were comparable to the concentration of paclitaxel found within the first 3 cm adjacent to the buttressed staple lines. These results suggest some active transport of paclitaxel to these sites, most likely through the lymphatic drainage system, which is also most often cited as the pathway for metastasis.

It will be understood that various modifications may be made to the embodiments disclosed herein. Therefore, the above description should not be construed as limiting, but merely as an exemplification of preferred embodiments. Those skilled in the art will envision other modifications within the scope and spirit of the present disclosure. Such modifications and variations are intended to come within the scope of the following claims.

What is claimed is:

1. A medical device comprising:
   a porous substrate; and
   a therapeutic layer having a thickness from about 11 nm to about 218 nm on at least a portion of the porous substrate, the therapeutic layer including a chemotherapeutic agent,
   wherein the therapeutic layer has a surface to volume ratio from about 500 mm$^{-1}$ to about 90,000 mm$^{-1}$.

2. The medical device of claim 1, wherein the chemotherapeutic agent is selected from paclitaxel and derivatives thereof, docetaxel and derivatives thereof, abraxane, tamoxifen, cyclophosphamide, actinomycin, bleomycin, dactinomycin, daunorubicin, doxorubicin, doxorubicin hydrochloride, epirubicin, mitomycin, methotrexate, fluorouracil, gemcitabine, gemcitabine hydrochloride, carboplatin, carmustine, methyl-CCNU, cisplatin, etoposide, camptothecin and derivatives thereof, phenesterine, vinblastine, vincristine, goserelin, leuprolide, interferon alfa, retinoic acid, nitrogen mustard alkylating agents, piposulfan, vinorelbine, irinotecan, irinotecan hydrochloride, vinblastine, pemetrexed, sorafenib tosylate, everolimus, erlotinib hydrochloride, sunitinib malate, capecitabine oxaliplatin, leucovorin calcium, bevacizumab, cetuximab, ramucirumab, trastuzumab, or combinations thereof.

3. The medical device of claim 1, wherein the chemotherapeutic agent includes a polymorph of paclitaxel.

4. The medical device of claim 3, wherein the polymorph of paclitaxel is selected from amorphous paclitaxel, crystalline paclitaxel dihydrate, anhydrous paclitaxel, or combinations thereof.

5. The medical device of claim 1, wherein the porous substrate has a pore volume from about 65% to about 85%.

6. The medical device of claim 1, wherein the therapeutic layer has a thickness from about from about 25 nm to about 75 nm.

7. The medical device of claim 1, wherein the therapeutic layer further comprises an excipient selected from 2-hydroxypropyl-beta-cyclodextrin, methyl-ß-cyclodextrin, sodium dodecyl sulfate, octylglucoside, sorbitan monooleate, sorbitan monolaurate, polyethoxylated fatty acid esters of sorbitan, oleic acid, citric acid, ascorbic acid, butylated hydroxytoluene, D-sorbitol, or combinations thereof.

8. The medical device of claim 1, wherein the medical device is selected from surgical buttresses, hernia patches, staples, tacks, stents, or tissue scaffolds.

9. A method for treating tissue comprising applying the medical device of claim 1 to tissue.

10. The method of claim 9, wherein applying the medical device to tissue occurs with a fixation device selected from staples, tacks, clips, sutures, adhesives, or combinations thereof.

11. A medical device comprising:
    a porous substrate; and
    a therapeutic layer having a thickness from about 25 nm to about 75 nm on at least a portion of the porous substrate, the therapeutic layer including a chemotherapeutic agent,
    wherein the therapeutic layer has a surface to volume ratio from about 500 mm$^{-1}$ to about 90,000 mm$^{-1}$.

12. The medical device of claim 11, wherein the chemotherapeutic agent is selected from paclitaxel and derivatives thereof, docetaxel and derivatives thereof, abraxane, tamoxifen, cyclophosphamide, actinomycin, bleomycin, dactinomycin, daunorubicin, doxorubicin, doxorubicin hydrochloride, epirubicin, mitomycin, methotrexate, fluorouracil, gemcitabine, gemcitabine hydrochloride, carboplatin, carmustine, methyl-CCNU, cisplatin, etoposide, camptothecin and derivatives thereof, phenesterine, vinblastine, vincristine, goserelin, leuprolide, interferon alfa, retinoic acid, nitrogen mustard alkylating agents, piposulfan, vinorelbine, irinotecan, irinotecan hydrochloride, vinblastine, pemetrexed, sorafenib tosylate, everolimus, erlotinib hydrochloride, sunitinib malate, capecitabine oxaliplatin, leucovorin calcium, bevacizumab, cetuximab, ramucirumab, trastuzumab, or combinations thereof.

13. The medical device of claim 11, wherein the chemotherapeutic agent includes a polymorph of paclitaxel.

14. The medical device of claim 13, wherein the polymorph of paclitaxel is selected from amorphous paclitaxel, crystalline paclitaxel dihydrate, anhydrous paclitaxel, or combinations thereof.

15. The medical device of claim 11, wherein the medical device has a pore volume from about 65% to about 85%.

16. The medical device of claim 11, wherein the therapeutic layer further comprises an excipient selected from 2-hydroxypropyl-beta-cyclodextrin, methyl-ß-cyclodextrin, sodium dodecyl sulfate, octylglucoside, sorbitan monooleate, sorbitan monolaurate, polyethoxylated fatty acid esters of sorbitan, oleic acid, citric acid, ascorbic acid, butylated hydroxytoluene, D-sorbitol, or combinations thereof.

17. A method for treating tissue comprising applying the medical device of claim 11 to tissue.

18. The method of claim 17, wherein applying the medical device to tissue occurs with a fixation device selected from staples, tacks, clips, adhesives, sutures, or combinations thereof.

19. A method of treating cancer, comprising:
introducing to a patient a surgical stapler having a buttress thereon, the buttress including a therapeutic layer on at least a portion of the buttress, the therapeutic layer having a thickness from about 11 nm to about 218 nm and a surface to volume ratio from about 500 $mm^{-1}$ to about 90,000 $mm^{-1}$; and
using the stapler to remove an undesired portion of an organ and emplace the buttress in a remaining portion of the organ, including stapling the buttress to tissue and cutting the tissue.

20. The method according to claim 19, wherein the stapler is used on the lung, and the therapeutic layer includes a chemotherapeutic agent.

* * * * *